United States Patent
Furukawa

(10) Patent No.: US 11,751,823 B2
(45) Date of Patent: Sep. 12, 2023

(54) IMAGE PROCESSING APPARATUS, IMAGE PROCESSING METHOD, AND PROGRAM

(71) Applicant: CANON KABUSHIKI KAISHA, Tokyo (JP)

(72) Inventor: Daisuke Furukawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 987 days.

(21) Appl. No.: 16/055,766

(22) Filed: Aug. 6, 2018

(65) Prior Publication Data
US 2019/0046127 A1    Feb. 14, 2019

(30) Foreign Application Priority Data
Aug. 9, 2017 (JP) ................. 2017-154671

(51) Int. Cl.
*A61B 6/03*  (2006.01)
*G06T 17/00*  (2006.01)
(Continued)

(52) U.S. Cl.
CPC ............. *A61B 6/03* (2013.01); *A61B 6/032* (2013.01); *A61B 6/5205* (2013.01);
(Continued)

(58) Field of Classification Search
CPC ......... A61B 6/03; A61B 6/5205; A61B 6/032; G06T 7/11; G06T 19/00; G06T 7/0012;
(Continued)

(56) References Cited

U.S. PATENT DOCUMENTS

2015/0187118 A1 * 7/2015 Masumoto ............. G06T 15/08
                                                                 345/419
2017/0035381 A1 * 2/2017 Madabhushi ........ A61B 6/5217
(Continued)

FOREIGN PATENT DOCUMENTS

JP    2009028161 A    2/2009
JP    2009273771 A  * 11/2009 ............... A61B 6/03

OTHER PUBLICATIONS

Wang et al. 2011 Clinical Imaging 35 184-192 (Year: 2011).*
(Continued)

*Primary Examiner* — Keith M Raymond
*Assistant Examiner* — Patrick M Mehl
(74) *Attorney, Agent, or Firm* — Canon U.S.A., Inc. IP Division

(57) ABSTRACT

A first extraction unit that extracts a region of a pulmonary nodule drawn in an image, a second extraction unit that extracts a region of a structure drawn in the image, a setting unit that sets a decision boundary to be at a position away from the pulmonary nodule region by a distance determined on a basis of a size of the pulmonary nodule region, a decision unit that decides whether or not the structure region extracted by the second extraction unit contacts with both a region related to the pulmonary nodule region and the decision boundary, and an acquisition unit that acquires, as a region of a desired structure, the structure region decided by the decision unit to contact with both the pulmonary nodule region and the decision boundary in the structure region extracted by the second extraction unit are included.

20 Claims, 22 Drawing Sheets

(51) Int. Cl.
*A61B 6/00* (2006.01)
*G06T 7/11* (2017.01)
*G06T 19/00* (2011.01)
*G06T 7/00* (2017.01)

(52) U.S. Cl.
CPC .............. *G06T 7/0012* (2013.01); *G06T 7/11* (2017.01); *G06T 17/005* (2013.01); *G06T 19/00* (2013.01); *G06T 2200/04* (2013.01); *G06T 2207/10081* (2013.01); *G06T 2207/30061* (2013.01); *G06T 2207/30101* (2013.01); *G06T 2210/41* (2013.01)

(58) Field of Classification Search
CPC .............. G06T 17/005; G06T 2210/41; G06T 2207/30101; G06T 2207/30061; G06T 2200/04; G06T 2207/10081
See application file for complete search history.

(56) References Cited

U.S. PATENT DOCUMENTS

2017/0039737 A1\* 2/2017 Madabhushi .......... G06V 10/44
2017/0140534 A1\* 5/2017 Chen .................... G06T 7/0012

OTHER PUBLICATIONS

Yim et al. 2005 CIARP 2005 LNCS 3773:654-662 (Year: 2005).\*
Hoffman https://www.webmd.com/lung/picture-of-the-trachea (Year: 2017).\*
Pechin Lo, et al., "Extraction of Airways From CT (Exact' 09)", IEEE Transactions on Medical Imaging, vol. 31, No. 11, Nov. 2012.

\* cited by examiner

FIG. 12
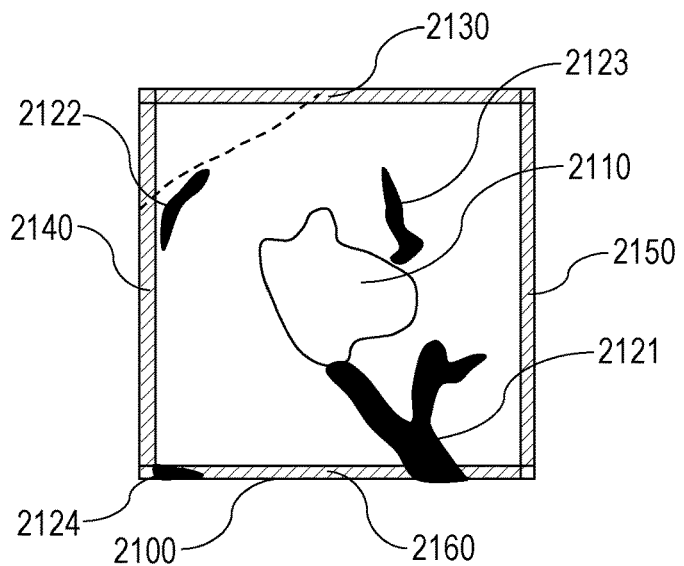
FIG. 13
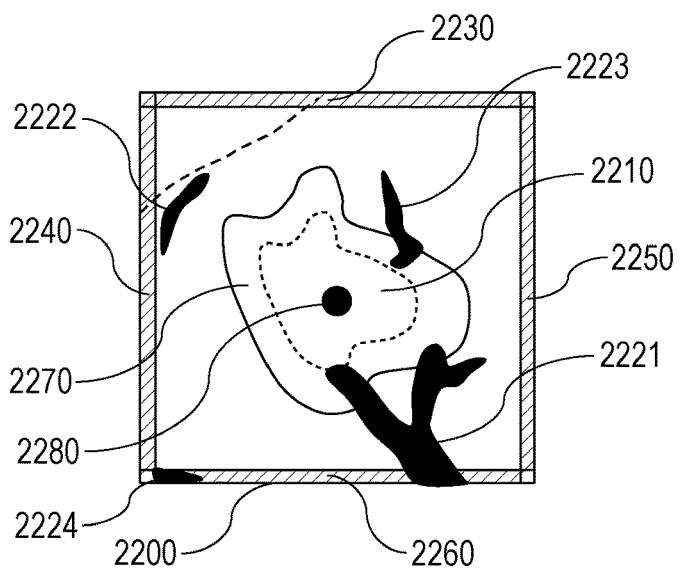
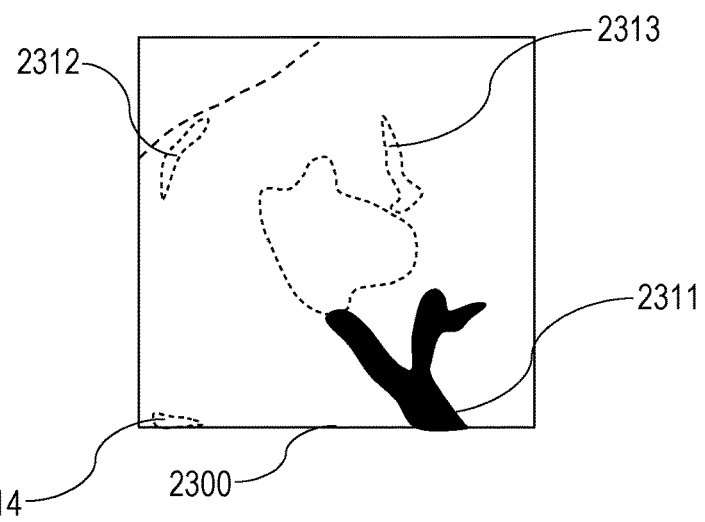

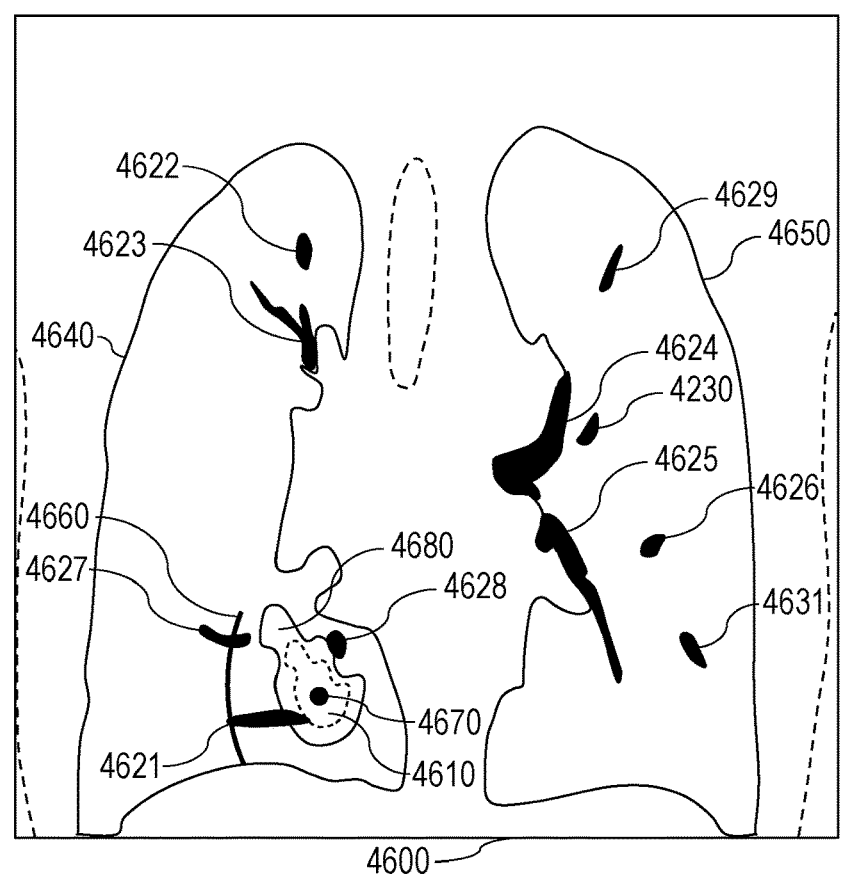
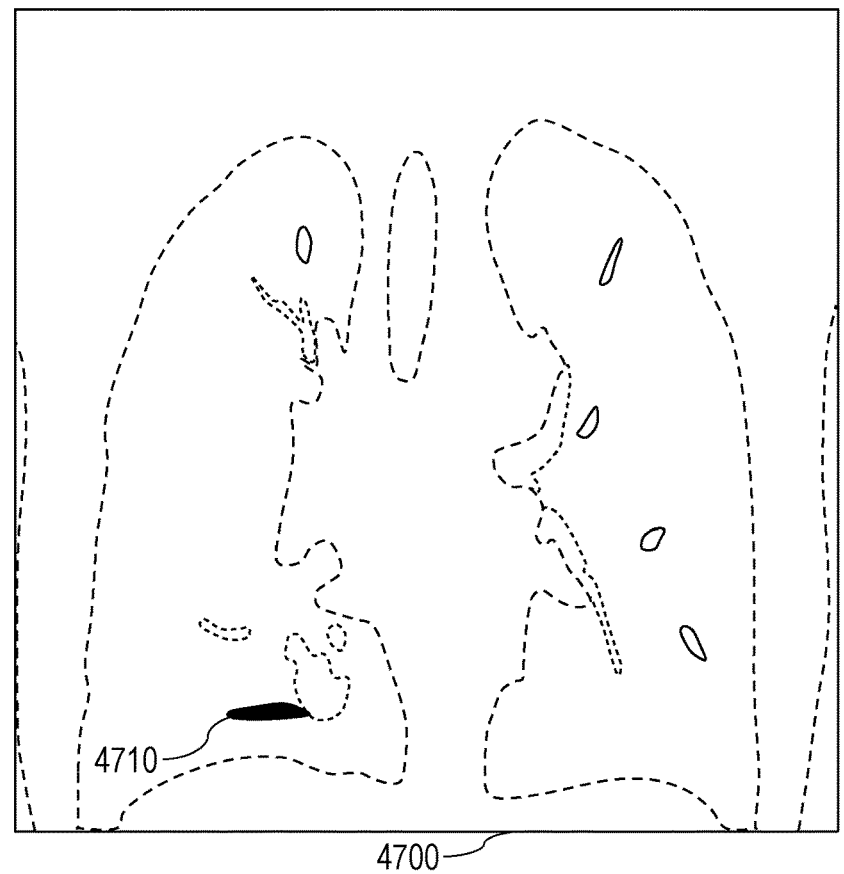
FIG. 26

IMAGE PROCESSING APPARATUS, IMAGE PROCESSING METHOD, AND PROGRAM

BACKGROUND OF THE INVENTION

Field of the Invention

A technique disclosed in the present disclosure relates to an image processing apparatus, an image processing method, and a program.

Description of the Related Art

Recently, with enhancement of high definition of a medical imaging apparatus such as a computed tomography apparatus (CT) or a nuclear magnetic resonance imaging apparatus (MRI), a number of images (medical images) have been captured from one patient. Accordingly, a load in work called radiological interpretation in which a doctor makes a diagnosis or examines a treatment policy on the basis of the medical images increases. This raises expectations for a system (Computer Aided Diagnosis: CAD) that analyzes medical images by a calculator and provides the doctor with information serving as an aid for the radiological interpretation.

As one of the work of radiological interpretation to be aided by the CAD system, differential diagnosis of a pulmonary nodule is cited. In differential diagnosis of a pulmonary nodule, in a case where a pulmonary nodule exists in a lung field region drawn in a chest X-ray CT image, whether the pulmonary nodule is benign or malignant is determined. For the determination, the doctor observes a state (image findings) of a bronchus or an artery and vein running around the pulmonary nodule (target pulmonary nodule) of interest. Then, the doctor determines whether the target pulmonary nodule is benign or malignant by using the state of the bronchus or the artery and vein, a state of another anatomical site, and a test result in combination.

To aid examination of image findings, which are carried out visually by the doctor, by using the calculator, the CAD system needs to extract a region of a bronchus or an artery and vein running around the target pulmonary nodule from a medical image. According to Pechin Lo, et al. "Extraction of Airways From CT (EXACT '09)", IEEE TRANSACTIONS ON MEDICAL IMAGING, VOL. 31, No. 11, November 2012, a plurality of kinds of image processing methods of extracting a region of a bronchus drawn in a medical image are disclosed. In the methods, all bronchi existing in a lung field region in a CT image are to be extracted. With the methods, regions of the bronchi are extracted by using such an anatomical feature that the bronchi form, with a trachea, a part of a structure having a tree structure. Specifically, with the methods, a region of a trachea is firstly extracted. Next, regions of first two bronchi (right and left main bronchi) connected to the trachea are extracted. Then, regions of a plurality of bronchi (lobar bronchi) connected to each of the main bronchi are extracted. While repeating such processing, extraction of regions is sequentially performed toward distal bronchi. Generally, the artery and vein running in a lung field is also extracted in a similar manner.

SUMMARY OF THE INVENTION

An image processing apparatus disclosed in the present disclosure includes a first extraction unit that extracts a region of a pulmonary nodule drawn in an image, a second extraction unit that extracts a region of a structure drawn in the image, a setting unit that sets a decision boundary to be at a position away from the pulmonary nodule region by a distance determined on a basis of a size of the pulmonary nodule region, a decision unit that decides whether or not the structure region extracted by the second extraction unit contacts with both a region related to the pulmonary nodule region and the decision boundary, and an acquisition unit that acquires, as a region of a desired structure, the structure region decided by the decision unit to contact with both the pulmonary nodule region and the decision boundary in the structure region extracted by the second extraction unit.

Further features of the present disclosure will become apparent from the following description of exemplary embodiments with reference to the attached drawings.

BRIEF DESCRIPTION OF THE DRAWINGS

FIG. 12 is a schematic view illustrating an example of a decision boundary set by the image processing apparatus according to the second embodiment.

FIG. 13 is a schematic view illustrating an example of decision processing performed by the image processing apparatus according to the second embodiment and a processing result thereof.

FIG. 26 is a schematic view illustrating an example of decision processing performed on the basis of the decision boundary set with use of the list $L_{42}$ by the image processing apparatus according to the fourth embodiment and an example of a processing result thereof.

DESCRIPTION OF THE EMBODIMENTS

Figure 1:
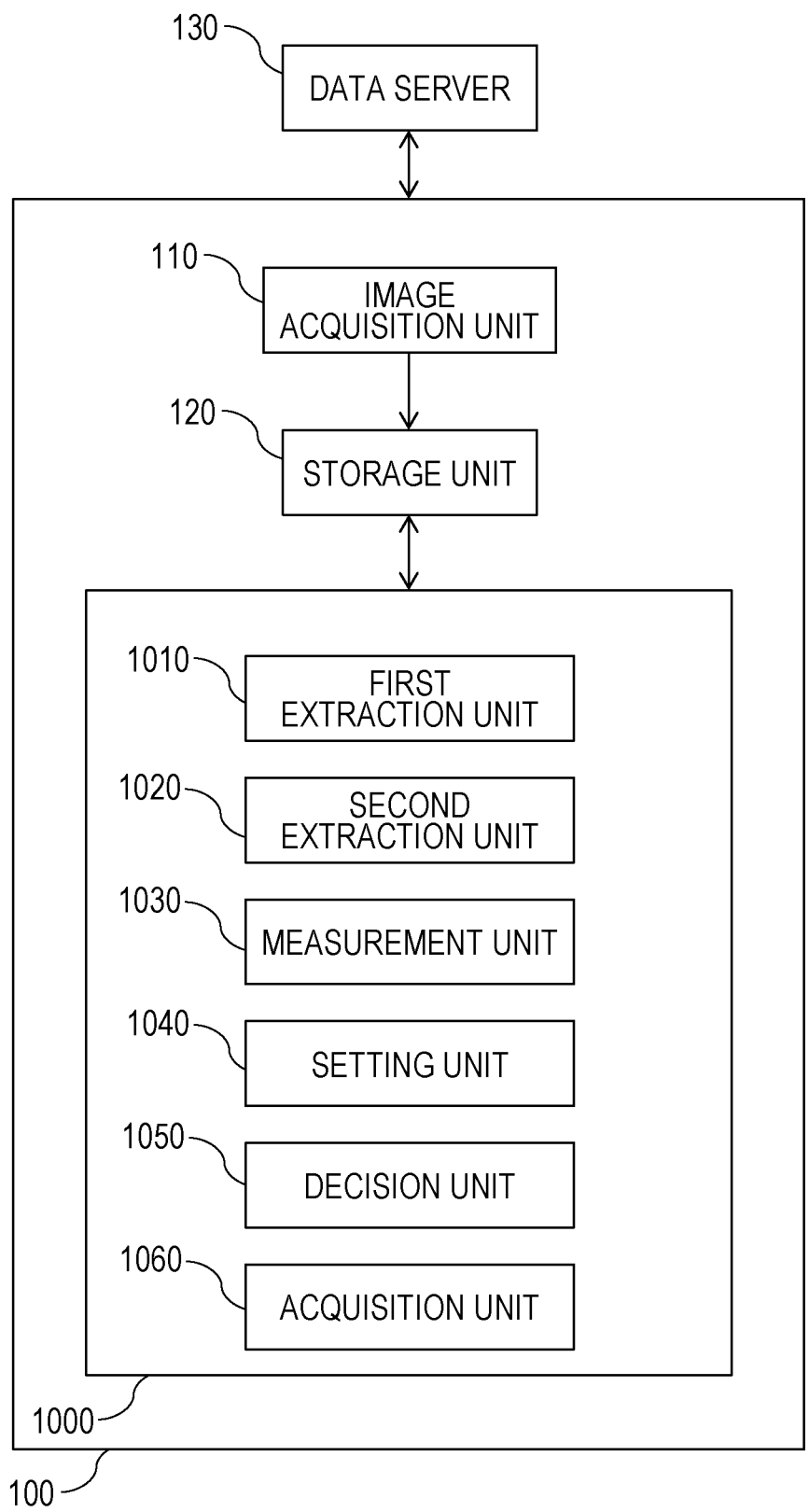
FIG. 1 illustrates an example of a functional configuration of an image processing apparatus according to a first embodiment.

A bronchus and an artery and vein are thin in diameter and contrast between the bronchus or the artery and vein and a lung field region there around is small. Since the bronchus or the artery and vein running around a heart moves during imaging due to influence of pulsation, blur is caused in an image thereof, so that the bronchus or the artery and vein is drawn being broken up in the image in some cases. Thus, with a technique described in Pechin Lo, et al. "Extraction of Airways From CT (EXACT '09)", IEEE TRANSACTIONS ON MEDICAL IMAGING, VOL. 31, No. 11, November 2012, a region of a bronchus or an artery and vein near a trachea or a large blood vessel is able to be extracted, but there is an issue that a region of a bronchus or an artery and vein running around a target pulmonary nodule is difficult to be extracted with high accuracy. Such an issue is to be solved by the present embodiment.

Hereinafter, embodiments will be described with reference to drawings. The same reference numerals are assigned to the same or equivalent components, members, and processing illustrated in the respective drawings, and repetitive description will be omitted as appropriate. Further, components, members, and processing that are not important from a descriptive point of view are partially omitted and are not illustrated in the respective drawings.

An example in which a three-dimensional chest CT image captured by an X-ray CT apparatus is processed will be described below. However, an application range of the present disclosure is not limited to the three-dimensional chest CT image. For example, the present disclosure is applicable also to a CT image in which an entire trunk of a body is imaged. The present disclosure is applicable also to an image captured by another imaging apparatus as long as being an image in which a nodule, a bronchus, or an artery and vein is visually recognized. The present disclosure is applicable also to a two-dimensional image or a three-dimensional image. Further, an embodiment of the present disclosure is not limited to the embodiments described below.

Embodiments of the present disclosure will be described below by taking extraction of a region of a bronchus as an example. However, the present disclosure is applicable also to extraction of a region of an artery and vein running in a lung field. Then, in a case where common processing is performed in extraction of the region of the bronchus and extraction of the region of the artery and vein, it is described that the common processing is performed, and in a case where different processing is performed therebetween, each content of the processing performed for each of them is described.

First Embodiment

An image processing apparatus according to the present disclosure extracts a structure (bronchus or artery and vein) running around a target pulmonary nodule. The structure running around the target pulmonary nodule has the following characteristics: (1) at least a part of a region of the structure to be extracted runs near the target pulmonary nodule, and (2) as a general feature of a structure region (region of a bronchus or an artery and vein), the structure region is neither broken up nor generated in a lung field except for disruption caused by a pulmonary nodule, pulsation, or the like. Thus, the structure to be extracted runs toward the target pulmonary nodule in a region away from the target pulmonary nodule by a fixed distance.

With attention to the foregoing points, the image processing apparatus according to the present disclosure firstly extracts a pulmonary nodule region and structure candidate regions (candidate regions of a bronchus or an artery and vein) in an image. Next, a decision boundary is set around the pulmonary nodule region. Then, whether or not each of the structure candidate regions passes through both a vicinity of the pulmonary nodule region and the decision boundary is decided. In a case where the structure candidate region passes through both the vicinity of the pulmonary nodule region and the decision boundary, the structure candidate region is acquired as a structure region related to the target pulmonary nodule. Otherwise, the structure candidate region is discarded.

In setting of the decision boundary, it is important that the decision boundary is arranged in a region where the structure (bronchus or artery and vein) runs toward the target pulmonary nodule. Meanwhile, the bronchus forms, with a trachea, a part of the structure having a tree structure. Therefore, the bronchus runs from almost a direction in which the trachea exists toward the target pulmonary nodule. Thus, when the bronchus running around the target pulmonary nodule is extracted, it is important that the decision boundary is arranged between the target pulmonary nodule and the trachea. Since an artery and vein in the lung field runs from a direction of an artery and vein in mediastinum toward the target pulmonary nodule, it is important that the decision boundary is arranged between the target pulmonary nodule and the artery and vein in the mediastinum in order to extract the artery and vein in the lung field.

In consideration of such a requirement for the arrangement of the decision boundary described above, the decision boundary is arranged so as to surround the target pulmonary nodule in a first embodiment. With such arrangement, regardless of the position of the target pulmonary nodule in the lung field region, the decision boundary is arranged in a region between the target pulmonary nodule and the trachea or the artery and vein in the mediastinum. It is also possible to extract a bronchus or an artery and vein that runs from a direction different from a direction of the trachea or the artery and vein in the mediastinum toward the target pulmonary nodule.

A functional configuration of the image processing apparatus according to the present embodiment will be described below with reference to FIG. 1. An image processing apparatus 100 includes an image acquisition unit 110, a storage unit 120, and an image processing unit 1000. The image processing unit 1000 further includes a first extraction unit 1010, a second extraction unit 1020, a measurement unit 1030, a setting unit 1040, a decision unit 1050, and an acquisition unit 1060. When at least one or more processors provided in the image processing apparatus 100 executes a program stored in at least one or more memories connected to the processors so as to allow communication, the image processing apparatus 100 functions as the image acquisition unit 110, the first extraction unit 1010, the second extraction unit 1020, the measurement unit 1030, the setting unit 1040, the decision unit 1050, and the acquisition unit 1060. Note that, any hardware such as a CPU (Central Processing Unit) or a GPU (Graphics Processing Unit) is able to be used for the processors. Processors of different types may be used in combination to realize each of the functions described above.

Further, a data server 130 for saving data to be input to the image processing apparatus 100 and data to be output by the image processing apparatus 100 is connected to the image processing apparatus 100 so as to allow communication.

The image acquisition unit 110 acquires an original image (three-dimensional chest CT image) from the data server 130. The acquired original image is saved in the storage unit 120.

The first extraction unit 1010 acquires the original image from the storage unit 120. By applying an image segmentation method (also called an image division method, a region segmentation method, or a region extraction method) that is one of known image processing methods to the original image, the first extraction unit 1010 extracts a region of a pulmonary nodule drawn in the original image. That is, the first extraction unit 1010 specifies a pixel belonging to the pulmonary nodule. Note that, the pixel specified by the first extraction unit 1010 is simply a pixel that is decided to be the pulmonary nodule by the first extraction unit 1010 and is not limited only to a pixel that indicates an actual pulmonary nodule.

With such processing, the first extraction unit 1010 acquires a masked image (pulmonary nodule masked image). Here, the masked image is a binary image and a pixel value of each of pixels indicates whether or not the pixel is a pixel belonging to a target region. That is, the pixel (pulmonary nodule pixel) that is specified as the pixel belonging to the pulmonary nodule by the image segmentation method is represented by a pixel value 1 and the other pixels (non-pulmonary nodule pixels) are represented by a pixel value 0. The acquired pulmonary nodule masked image is saved in the storage unit 120.

Any value may be given as the pixel value of the masked image as long as a pixel indicating a region (a pulmonary nodule region in the pulmonary nodule masked image) of a target object is distinguishable from the other pixels. For example, either 1 or 2 may be given as the pixel value. The pixel indicating the region of the target object and the other pixels each may be given any one of a plurality of values that are different from each other.

Though the aforementioned masked image is the binary image, a multi-value masked image is used when there are a plurality of target objects. For example, in a case where there are N target objects, N+1-value masked image is used. At this time, each pixel of the masked image has any one of N+1 pixel values. Here, the pixel value may be any value as long as each of regions of the target objects is distinguishable from the other regions.

The characteristics of the binary and multi-value masked images described above are also applied similarly to all masked images used in the present disclosure.

The second extraction unit 1020 acquires the original image from the storage unit 120. By applying the known image segmentation method to the original image, the second extraction unit 1020 extracts a region of a bronchus drawn in the original image. That is, the second extraction unit 1020 specifies a pixel belonging to the bronchus. Note that, the pixel specified by the second extraction unit 1020 is simply a pixel that is decided to be the bronchus by the second extraction unit 1020 and is not limited only to a pixel that indicates an actual bronchus.

In the processing performed by the second extraction unit 1020, a plurality of regions are normally extracted. The regions include a region of the bronchus running around the target pulmonary nodule, a region of a bronchus running in a place away from the target pulmonary nodule, and a region that does not indicate a bronchus (that is erroneously extracted). Here, according to the image processing apparatus according to the present embodiment, it is considered that a desired region (the region of the bronchus running around the target pulmonary nodule) and other regions are extracted in second extraction processing. Thus, each region extracted in the second extraction processing is called a candidate region of the bronchus running around the target pulmonary nodule. Hereinafter, the region is called a candidate region more simply.

By applying the known segmentation method to the original image, the second extraction unit 1020 acquires a masked image (candidate masked image). In the acquired candidate masked image, a pixel (candidate pixel) specified as a pixel belonging to a candidate region is represented by a pixel value 1 and the other pixels (non-nodule pixels) are represented by a pixel value 0. Though the pixel values are used also in the pulmonary nodule masked image, there is no problem because the masked images are different from each other. The acquired candidate masked image is saved in the storage unit 120. Note that, any value may be given as the pixel value as long as a candidate pixel is distinguishable from a pixel other than the candidate pixel in the candidate masked image.

The measurement unit 1030 acquires the pulmonary nodule masked image from the storage unit 120. Then, the measurement unit 1030 measures a coordinate value of a centroid position and an average radius of the pulmonary nodule region in the pulmonary nodule masked image. The coordinate value of the centroid position and a value of the average radius that are measured are saved in the storage unit 120.

The setting unit 1040 carries out two different processing. In the first processing, a composite masked image is generated. The composite masked image is a masked image generated by overlapping the pulmonary nodule masked image and the candidate masked image. In the composite masked image, a pixel that has the same coordinate value as that of the pulmonary nodule pixel in the pulmonary nodule masked image is also a pulmonary nodule pixel. Similarly, a pixel having the same coordinate value as that of the candidate pixel in the candidate masked image is also a candidate pixel.

The other processing performed by the setting unit 1040 is processing for setting a decision boundary in the composite masked image. The decision boundary and detailed setting processing thereof will be described in explanation for step S1060. The composite masked image generated by the setting unit 1040 is saved in the storage unit 120.

The decision unit 1050 acquires the composite masked image from the storage unit 120. Then, the decision unit 1050 decides whether or not each of candidate regions in the composite masked image is a desired region. The decision processing is performed by using the decision boundary set in the composite masked image. A decision result is saved in the storage unit 120. Here, the desired region is, for example, a region of the bronchus running around the target pulmonary nodule, but is not limited thereto.

The acquisition unit 1060 acquires, from the storage unit 120, the composite masked image and the decision result by the decision unit 1050. The acquisition unit 1060 acquires a desired region from among the candidate regions in the composite masked image on the basis of the decision result. The acquisition unit 1060 saves information of the acquired desired region in a format of a masked image (bronchus masked image). The bronchus masked image is saved in the data server 130 via the storage unit 120.

Figure 3:
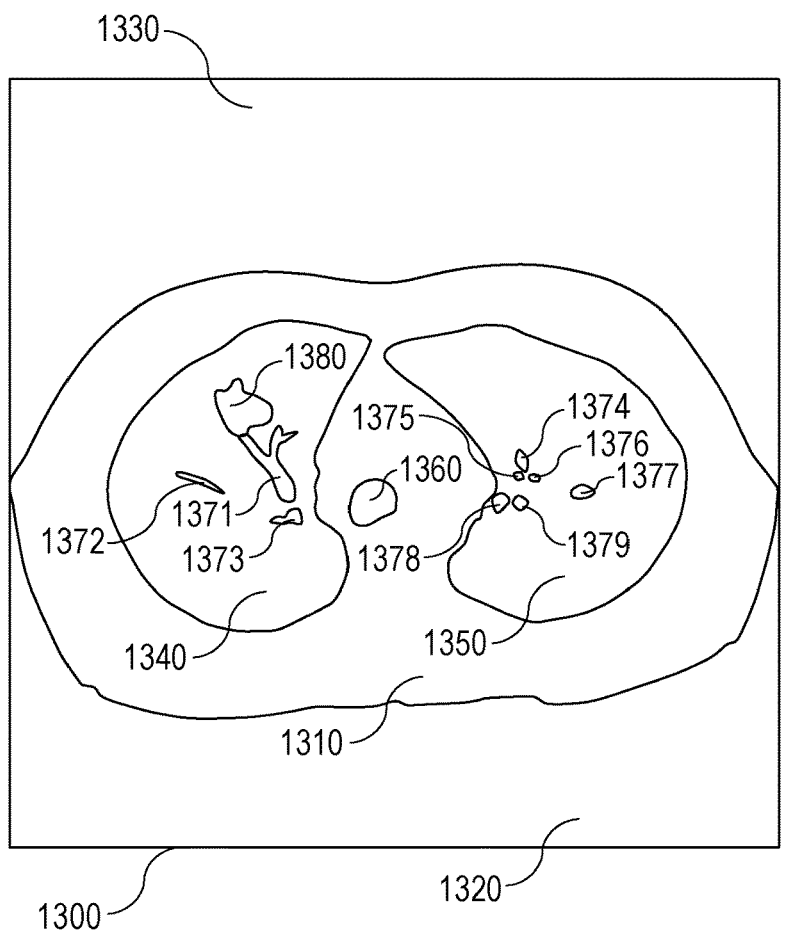
FIG. 3 illustrates an example of an original image processed by an image processing apparatus according to a first or second embodiment.

With reference to FIG. 3, an original image processed by the image processing apparatus 100 according to the present embodiment will be described. An image 1300 of FIG. 3 is one cross-sectional image of a plurality of cross-sectional (axial cross-sectional) images that constitute a three-dimensional chest CT image (original image). Though FIG. 3 illustrates one representative cross-sectional image in the original image due to limitation of a drawing, the original image includes many cross-sectional images. Though FIG. 3 illustrates an example in which the original image is constituted by an axial cross-sectional image for ease of understanding, the original image may be constituted by a different cross-sectional image (for example, a coronal cross-sectional image or a sagittal cross-sectional image).

A torso 1310 of a patient, an air region 1320 and an air region 1330 around the torso are captured in the original image 1300. Further, a right lung 1340 and a left lung 1350 exist in the torso 1310. It is to be noted that, in the CT image, the right lung is captured on a left side of the image and the left lung is captured on a right side of the image. A trachea 1360 exists in the center of the torso 1310. Bronchi 1371 to 1379 exist in the right lung 1340 and the left lung 1350. The bronchi form a three-dimensional tubular structure (inside of which forms a thick linear structure) and are connected to the trachea 1360 by a tomographic image (not illustrated). A pulmonary nodule 1380 exists in the right lung 1340. In FIG. 3, since a region of the bronchus 1371 extends toward the nodule, the region of the bronchus 1371 is a region of a bronchus running around a target pulmonary nodule. That is, the region of the bronchus 1371 is a bronchus region (desired bronchus region) that is desired to be extracted in the present embodiment.

Figure 2:
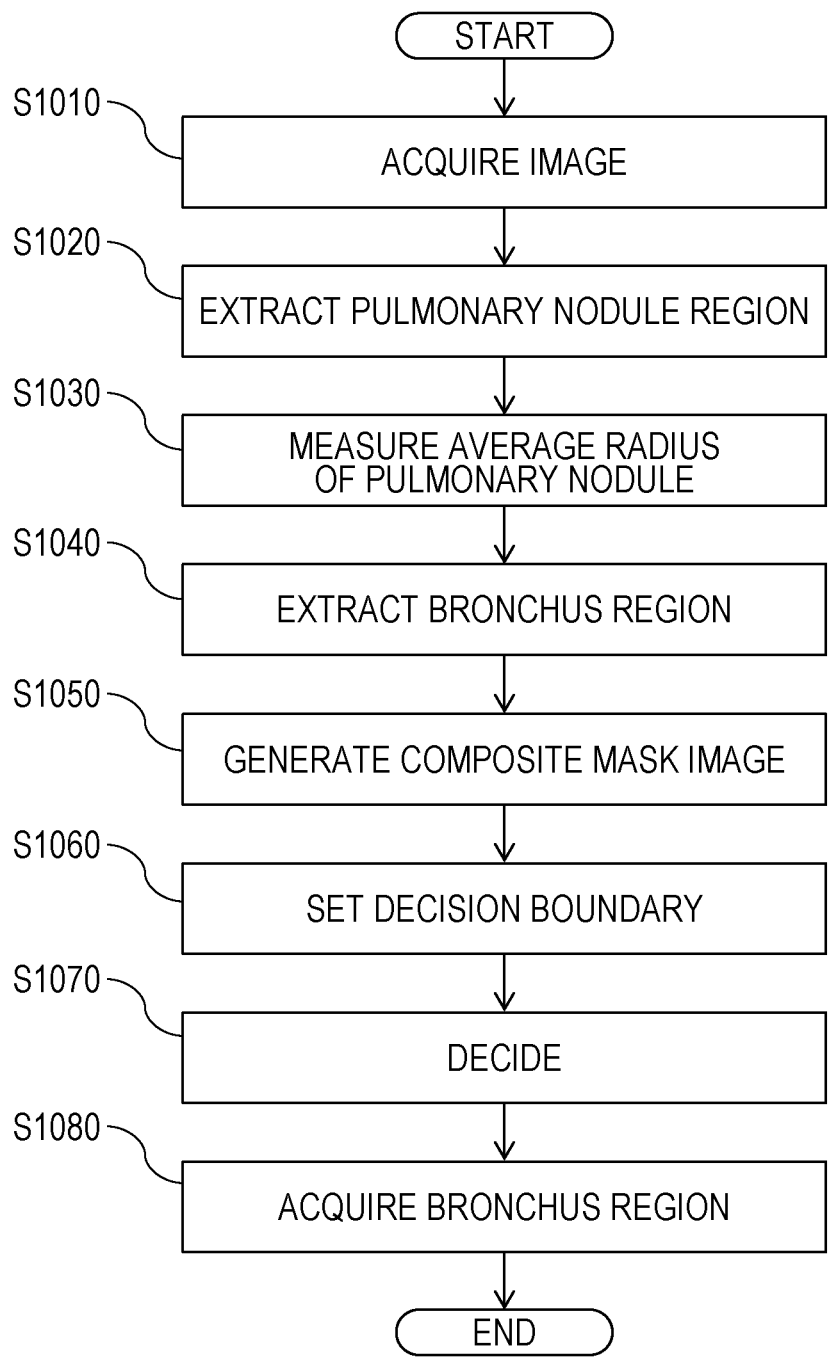
FIG. 2 is a flowchart illustrating an example of processing procedure of the image processing apparatus according to the first embodiment.

Next, processing procedure of the image processing apparatus 100 of the present embodiment will be described with reference to FIG. 2.

(S1010)

At step S1010, the image acquisition unit 120 acquires the original image from the data server 130. The acquired original image is saved in the storage unit 120.

(S1020)

At step S1020, the first extraction unit 1010 acquires the original image from the storage unit 120. The first extraction unit 1010 extracts a region (pulmonary nodule region) of a pulmonary nodule that exists in the original image. The pulmonary nodule region has an almost constant CT value in a CT image. Thus, by using a known image segmentation method (such as a threshold processing method, a region extension method, a level-set method, or a graph-cut method), the pulmonary nodule region is able to be extracted.

Note that, a pointing device attached to the image processing apparatus 100 is also able to be used to extract the pulmonary nodule region. For example, an operator is caused to designate a position of the pulmonary nodule existing in the original image by a mouse. When the operator designates the position of the pulmonary nodule, the first extraction unit 1010 acquires a coordinate value of the position designated by the operator. Then, a position coordinate that is acquired is used as input information (for example, a region extension start point in the region extension method) to the image segmentation method. In this manner, the pulmonary nodule region is able to be extracted with high accuracy.

The first extraction unit 1010 saves information of the extracted pulmonary nodule region in a format of a masked image (pulmonary nodule masked image). The pulmonary nodule masked image is saved in the storage unit 120.

Figure 4:
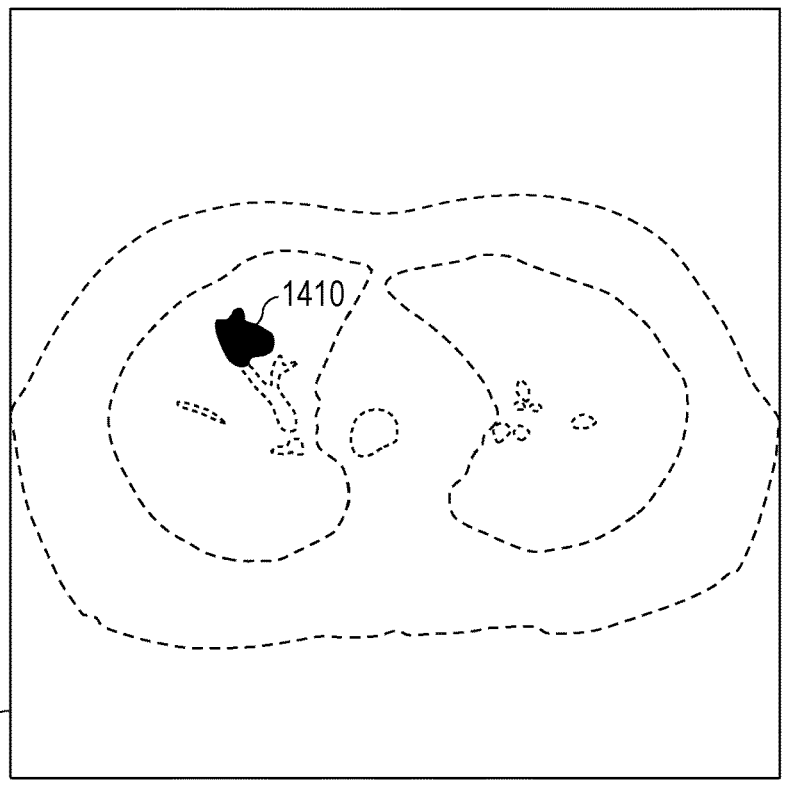
FIG. 4 is a schematic view illustrating an example of a pulmonary nodule region extracted from the original image.

FIG. 4 illustrates an example of an extraction result of the pulmonary nodule region. An image 1400 of FIG. 4 is a pulmonary nodule masked image $M^{nodule}$ that is obtained by applying the processing of the present step to the original image 1300 of FIG. 3. A region 1410 in the pulmonary nodule masked image 1400 is a pulmonary nodule region $V^{nodule}$. This region corresponds to the pulmonary nodule 1380 existing in the right lung 1340 in the original image 1300. As illustrated in FIG. 4, the pulmonary nodule region is able to be extracted generally well through the processing of the present step.

(S1030)

At step S1030, the measurement unit 1030 measures an average radius of the pulmonary nodule region $V^{nodule}$. First, the measurement unit 1030 acquires the pulmonary nodule masked image $M^{nodule}$ from the storage unit 120.

Then, the measurement unit 1030 calculates a coordinate value of a centroid position of the pulmonary nodule region $V^{nodule}$ in the pulmonary nodule masked image. Here, a coordinate value of a pixel belonging to the pulmonary nodule region $V^{nodule}$ is set as $P^{nodule}_{[i]} = (x^{nodule}_{[i]}, y^{nodule}_{[i]}, z^{nodule}_{[i]})$. In this case, $i=1, \ldots, \#(V^{nodule})$, and $\#(V^{nodule})$ indicates the number of pixels belonging to $V^{nodule}$. Then, a coordinate value $G^{nodule} = (G^{nodule}_x, G^{nodule}_y, G^{nodule}_z)$ of the centroid position is calculated by a mathematical formula 1.

$$(G^{nodule}_x, G^{nodule}_y, G^{nodule}_z) = \frac{1}{\#(V^{nodule})} \sum_{i=1}^{\#(V^{nodule})} (x^{nodule}_{[i]}, y^{nodule}_{[i]}, z^{nodule}_{[i]})$$

After calculating the coordinate value $G^{nodule}$ of the centroid position, the measurement unit 1030 measures an average radius $R^{nodule}$ of the pulmonary nodule region. Here, a set of pixels adjacent to a non-pulmonary nodule pixel among pixels (pulmonary nodule pixels) belonging to the pulmonary nodule region $V^{nodule}$ is set as $S^{nodule}$. Then, the average radius $R^{nodule}$ is calculated by a mathematical formula 2.

$$R^{nodule} = \frac{1}{\#(S^{nodule})} \sum_{i=1}^{\#(S^{nodule})} \sqrt{(x_{[i]}^{nodule} - G_x^{nodule})^2 + (y_{[i]}^{nodule} - G_y^{nodule})^2 + (z_{[i]}^{nodule} - G_z^{nodule})^2}$$

Here, $\#(S^{nodule})$ indicates the number of pixels belonging to $S^{nodule}$.

Note that, there is a case where the average radius of the pulmonary nodule region drawn in the original image is known by some method before the image processing apparatus 100 of the present embodiment starts processing. An example thereof includes a case where the operator limits a size of the pulmonary nodule to be processed by the image processing apparatus 100 of the present embodiment to a constant size in advance. In such a case, the measurement unit 1030 may not perform calculation of the average radius of the pulmonary nodule region indicated by the mathematical formula 2 and may set a value $R^{nodule}_{known}$ as the average radius $R^{nodule}$ instead. Here, $R^{nodule}_{known}$ is a known average radius of the pulmonary nodule region drawn in the original image. Before the image processing apparatus 100 of the present embodiment starts processing, $R^{nodule}_{known}$ is stored in the data server 130. At step S1030, the measurement unit 1030 acquires $R^{nodule}_{known}$ from the data server 130. The measurement unit 1030 then sets the acquired constant of $R^{nodule}_{known}$ as the average radius $R^{nodule}$.

The coordinate value $G^{nodule}$ of the centroid position and the average radius $R^{nodule}$ of the pulmonary nodule region that are calculated are saved in the storage unit 120 (S1040).

At step S1040, the second extraction unit 1020 extracts candidate regions of the bronchus existing in the original image.

The second extraction unit 1020 acquires the original image from the storage unit 120. The second extraction unit 1020 extracts the bronchus candidate regions by using a known image segmentation method. A method in which a method using eigen values of a Hesse matrix and a region extension method are combined will be described below.

First, the second extraction unit 1020 calculates a Hesse matrix for each pixel in the original image. The Hesse matrix is a 2×2 square matrix when the original image is a two-dimensional image and is a 3×3 square matrix when the original image is a three-dimensional image. A value of each element in the Hesse matrix at a pixel p of an original image $I^{input}$ is a value of the pixel p of a second order partial derivative of $I^{input}$.

The second extraction unit 1020 calculates the Hesse matrix for each pixel p of the original image $I^{input}$ and then calculates three eigen values $E_1(p)$, $E_2(p)$, and $E_3(p)$ (here, $E_3(p) > E_2(p) > E_1(p)$) of the Hesse matrix of each pixel. The second extraction unit 1020 further calculates a value $L^{line}(p)$ defined by the following mathematical formula 3.

$$L^{line}(p) = \begin{cases} |E_3(p)| \varphi(E_2(p); E_3(p)) \omega(E_1(p); E_2(p)) & (E_3(p) > E_2(p) > 0) \\ 0 & \text{otherwise} \end{cases}$$

Here, $\varphi$ and $\omega$ are respectively calculated by mathematical formulas 4 and 5.

$$\varphi(E_2(p); E_3(p)) = \begin{cases} \left(\frac{E_2(p)}{E_3(p)}\right)^\gamma & (E_3(p) > E_2(p) > 0) \\ 0 & \text{otherwise} \end{cases}$$

$$\omega(E_1(p); E_2(p)) = \begin{cases} \left(1 + \frac{E_1}{|E_2|}\right)^\gamma & (E_2(p) > E_1(p) > 0) \\ \left(1 + \alpha \frac{E_1}{|E_2|}\right)^\gamma & \left(-\frac{|E_2|}{\alpha} < E_1 < 0\right) \\ 0 & \text{otherwise} \end{cases}$$

When a linear structure is drawn in the original image, $L^{line}(p)$ has a large value at the pixel p in a region of the linear structure. Here, a bronchus has a tubular structure but has characteristics that an inside of the bronchus is drawn as a thick linear structure in the original image. Thus, by applying threshold processing ($I^{input}(p) < T^{input}_1$ and $L^{line}(p) > T^{line}$) to the original image and $L^{line}(p)$ calculated for each pixel of the original image, a pixel that is likely to belong to the bronchus region in the original image is able to be acquired. Note that, thresholds $T^{input}_1$ and $T^{line}$ may be obtained by setting the thresholds so that highest extraction accuracy of the bronchus region is achieved when the bronchus region is extracted by applying the image processing described in the present step to a learning image of the same type as the original image.

After finishing the processing described above, the second extraction unit 1020 applies the region extension method to the original image and extracts the bronchus candidate region. The extension start point is set as the pixel that is likely to belong to the bronchus region in the original image acquired by the processing described above. A condition of the extension is that a pixel value $I^{input}(p')$ of a pixel p' within a radius $RG_1$ with an extension candidate pixel p as the center is smaller than a threshold $T^{input}_2$ ($I^{input}(p') < T^{input}_2$) Note that, the radius $RG_1$ and the threshold value $T^{input}_2$ may be obtained by setting the radius and the threshold so that the highest extraction accuracy of the bronchus region is achieved when the bronchus candidate region is extracted by applying the image processing described in the present step to a learning image of the same type as the original image.

The second extraction unit 1020 saves information of the extracted candidate region in a format of a masked image (candidate region masked image $M^{candidate}$). The candidate region masked image is saved in the storage unit 120.

Figure 5:
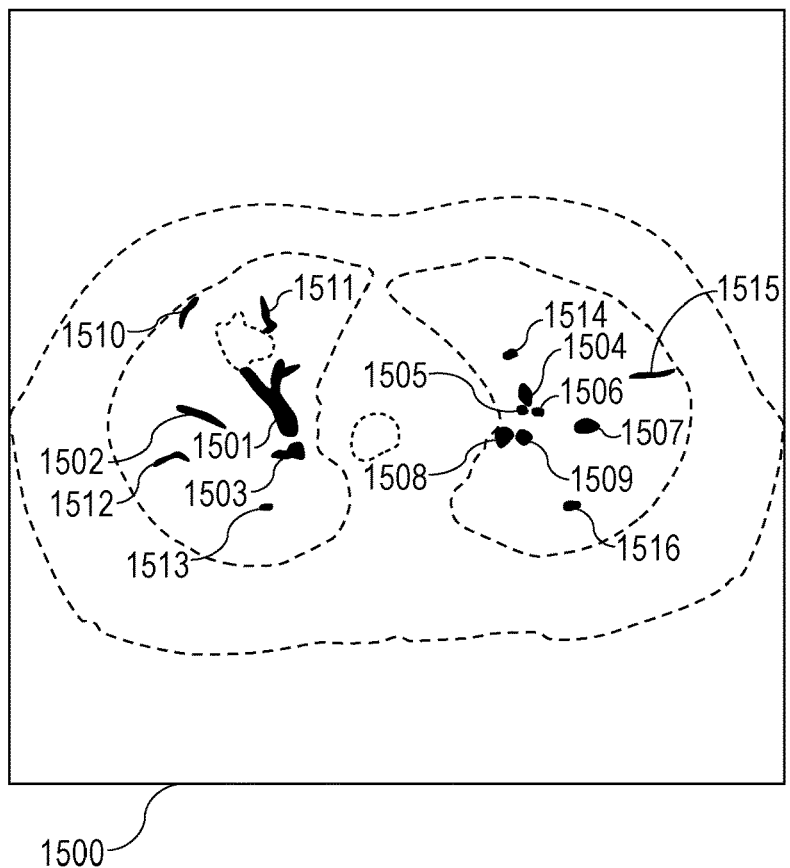
FIG. 5 is a schematic view illustrating an example of a candidate region of a bronchus extracted from the original image.

FIG. 5 illustrates an example of an extraction result of the bronchus candidate region. An image 1500 of FIG. 5 is a candidate masked image $M^{candidate}$ that is obtained by applying the processing of the present step to the original image 1300 of FIG. 3. Regions 1501 to 1516 in the candidate masked image 1500 are bronchus candidate regions $V^{candidate}_{[i]}$. Among the regions, the regions 1501 to 1509 correspond to the bronchi 1371 to 1379 existing in the right lung 1340 and the left lung 1350 in the original image 1300. As illustrated in FIG. 5, the bronchus region is able to be extracted generally well through the processing of the present step. However, it is to be noted that the regions extracted by the processing described above may include a (erroneously extracted) region other than the bronchus. The regions 1510 to 1516 in the image 1500 are such erroneously extracted regions. In the processing described above, parameters that achieve the highest extraction accuracy of the bronchus region in a learning image are used for parameters $I^{input}_1$, $T^{line}$, $R^{RG}_1$, and $T^{input}_2$. However, even when optimum parameters are used, a region other than the bronchus is erroneously extracted as the bronchus candidate region in some cases. Thus, the image processing apparatus 100 according to the present embodiment excludes such a region other than the bronchus by processing in the following stage. In view of such a point, the regions (regions 1501 to 1516 in the image 1500) extracted at step S1040 are called candidate regions.

Finally, though information of a lung filed region is not used for the extraction of the candidate regions in the processing described above, the second extraction unit 1020 may use information of the lung field region to extract the candidate regions. In this case, the second extraction unit 1020 extracts the lung field region in the original image by using a known image segmentation method. Then, the second extraction unit 1020 limits a processing range at the present step to the lung field region. Thereby, the candidate regions to be extracted are limited to the inside of the lung field region, so that it is possible to improve a processing speed and extract the bronchus region with high accuracy. (S1050)

At step S1050, the setting unit 1040 generates a composite masked image $M^{composite1}$. The composite masked image $M^{composite}_1$ is a ternary masked image and respective pixels take three values of 0, 1, and 2. Here, the pixel value 1 indicates that the pixel is a pixel belonging to the pulmonary nodule region. The pixel value 2 indicates that the pixel is a pixel belonging to the candidate region. The pixel value 0 indicates that the pixel is a pixel belonging to neither the pulmonary nodule region nor the candidate region. Note that, the pixel values are not limited to the aforementioned values. Pixels whose pixel values are values of 1, 2, and 0 in the composite masked image $M^{composite1}$ are respectively called a pulmonary nodule pixel, a candidate pixel, and a background pixel.

First, the setting unit 1040 acquires a pulmonary nodule masked image $M^{nodule}$ and a candidate region masked image $M^{candidate}$ from the storage unit 120. Next, the setting unit 1040 generates a composite masked image $M^{composite1}$ with the same image size as those of the images. When generating the composite masked image $M^{composite1}$, first, the setting unit 1040 sets all the pixels as background pixels (that is, sets pixel values to 0).

After generating the composite masked image $M^{composite1}$, the setting unit 1040 searches for pixels of the composite masked image $M^{composite1}$ that have the same coordinate values as those of pixels belonging to the pulmonary nodule region $V^{nodule}$ of the pulmonary nodule masked image $M^{nodule}$ and sets pixel values of the pixels to 1. Further, the setting unit 1040 searches for pixels of the composite masked image $M^{composite1}$ that have the same coordinate values as those of pixels belonging to the candidate region $V^{candidate}$ of the candidate region masked image $M^{candidate}$ and sets pixel values of the pixels to 2.

Figure 6:
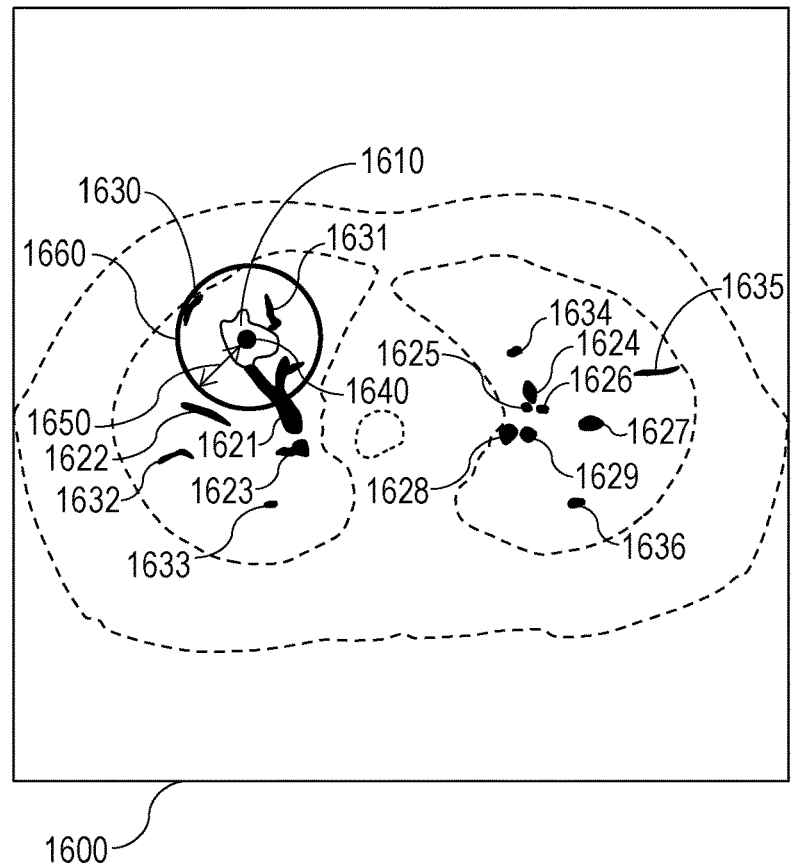
FIG. 6 is a schematic view for explaining an example of a decision boundary set by the image processing apparatus according to the first embodiment.

FIG. 6 illustrates an example of the composite masked image $M^{composite1}$ generated by the setting unit 1040. An image 1600 of FIG. 6 is one cross-sectional image of the composite masked image $M^{composite1}$. The cross-sectional image is a cross-sectional image seen from the same position as that of the image 1300 of FIG. 3. A region 1610 in the image 1600 is a region corresponding to the pulmonary nodule region $V^{nodule}$ (the pulmonary nodule region 1410 in FIG. 4) of the pulmonary nodule masked image $M^{nodule}$. Regions 1621 to 1636 are regions corresponding to the candidate regions $V^{candidate}_{[i]}$ ($1<=i<N^{candidate}$) (candidate regions 1501 to 1516 in FIG. 5) of the candidate region masked image $M^{candidate}$. Note that, a black point 1640, an arrow 1650, and a closed curve 1660 are information applied at next step S1060, so that description thereof will be omitted.

Hereinafter, the region 1610 in the image 1600 (composite masked image $M^{composite1}$) is also called a pulmonary nodule region $V^{nodule}$ similarly to the pulmonary nodule region of the pulmonary nodule region masked image $M^{nodule}$. Moreover, the regions 1621 to 1636 are also called candidate regions $V^{candidate}_{[i]}$ similarly to the candidate region of the candidate region masked image $M^{candidate}$. (S1060)

At step S1060, the setting unit 1040 sets a decision boundary. The decision boundary will be specifically described continuously with reference to FIG. 6.

At step S1060, the setting unit 1040 sets the decision boundary to the composite masked image $M^{composite1}$. The decision boundary is arranged at a position away from the centroid position of the pulmonary nodule region by a fixed distance. That is, the decision boundary has a shape equivalent to that of a surface of a sphere having a predetermined radius with the centroid position of the pulmonary nodule region as the center. The closed curve 1660 in FIG. 6 is the decision boundary set by the setting unit 1040. In FIG. 6, since only one cross-sectional image of the composite masked image $M^{composite1}$ is illustrated, the decision boundary 1660 appears to have a round shape, but when all cross-sectional images of the composite masked image $M^{composite1}$ are cross-sectionally observed, it is found that the decision boundary 1660 has a spherical shape.

In order to arrange the decision boundary in the composite masked image $M^{composite1}$, the setting unit 1040 determines a center of the decision boundary and a radius of the decision boundary. First, the setting unit 1040 determines the center of the decision boundary. The center of the decision boundary is set as the centroid position of the pulmonary nodule region 1610. The coordinate value $G^{nodule}$ of the centroid position of the pulmonary nodule region has been already calculated at step S1030 and saved in the storage unit 120. Thus, the setting unit 1040 acquires the coordinate value $G^{nodule}$ of the centroid position of the pulmonary nodule region from the storage unit 120. The acquired value is used as the coordinate value of the center of the decision boundary. In FIG. 6, the black point 1640 is the centroid position of the pulmonary nodule region $V^{nodule}$. According to a positional relationship between the centroid position 1640 of the pulmonary nodule region $V^{nodule}$ and the decision boundary 1660, it is found that the center of the decision boundary 1660 matches the centroid position 1640 of the pulmonary nodule region $V^{nodule}$.

Next, the setting unit 1040 determines the radius of the decision boundary. The radius of the decision boundary is determined on the basis of an average radius of the pulmonary nodule region, for example. Specifically, one value corresponding to the average radius $R^{nodule}$ of the pulmonary nodule region $V^{nodule}$ is selected from among a plurality of values prepared in advance and the selected value is set as the radius of the decision boundary. In the composite masked image 1600 of FIG. 6, the arrow 1650 indicates the radius of decision boundary. The radius of the decision boundary may be determined on the basis of information (such as an average diameter, a maximum radius, a median value of the radius) other than the average radius of the pulmonary nodule region.

The average radius $R^{nodule}$ of the pulmonary nodule region $V^{nodule}$ has been calculated at step S1030 and saved in the storage unit 120. Then, the setting unit 1040 acquires the average radius $R^{nodule}$ of the pulmonary nodule region from the storage unit 120. Next, the setting unit 1040 acquires, via the storage unit 120 from the data server 130, a list $L_1$ in which radiuses of the pulmonary nodule region are stored. In the list $L_1$, a plurality of sets of two numerical values of (average radius $R^{nodule}_{[k]}$ of pulmonary nodule region, radius $R^{decision}_{[k]}$ of decision boundary) ($1<=k<=N^{L1}$) are stored. For example, a plurality of radiuses $R^{decision}_{[k]}$ of the decision boundary that have different values are associated with a plurality of average radiuses $R^{nodule}_{[k]}$ having different values. Here, $R^{decision}_{[k]}$ is a radius of the decision boundary by which a desired bronchus region is able to be extracted with the highest accuracy in an image in which a pulmonary nodule region whose average radius is $R^{nodule}_{[k]}$ is drawn. Note that, $R^{decision}_{[k]}$ may be a value by which a desired bronchus region is able to be extracted with the accuracy of a given threshold or more in an image in which a pulmonary nodule region whose average radius is $R^{nodule}_{[k]}$ is drawn.

After acquiring the list $L_1$ from the data server 130, the setting unit 1040 compares each $R^{nodule}_{[k]}$ stored in $L_1$ to $R^{nodule}$ and searches for a value $R^{nodule}_{[k']}$ ($1<=k'<=N^{L1}$) closest to $R^{nodule}$. A radius $R^{decision}_{[k']}$ of the decision boundary that is paired with $R^{nodule}_{[k']}$ is used as the radius of the decision boundary to be set to the composite masked image $M^{composite1}$.

Note that, there is a case where the average radius of the pulmonary nodule region drawn in the original image is known by some method before the image processing apparatus 100 of the present embodiment starts processing. An example thereof includes a case where the operator limits a size of the pulmonary nodule to be processed by the image processing apparatus 100 of the present embodiment to a constant size in advance. In such a case, the setting unit 1040 may set a constant $R^{decision}_{const}$ as the radius of the decision boundary instead of performing the aforementioned processing for determining the radius of the decision boundary. Here, a known average radius of the pulmonary nodule drawn in the original image is set as $R^{nodule}_{known}$. Then, the constant $R^{decision}_{const}$ may have a value by which a desired bronchus region is able to be extracted with the accuracy of a given threshold or more in an image in which a pulmonary nodule region whose average radius is $R^{nodule}_{known}$ is drawn. The constant $R^{decision}_{const}$ is stored in the data server 130 before the image processing apparatus 100 of the present embodiment starts processing. At step S1060, the setting unit 1040 acquires $R^{decisiom}_{const}$ from the data server 130. The setting unit 1040 sets the acquired constant $R^{decision}_{const}$ as the radius of the decision boundary. As described above, also when a size of the pulmonary nodule is known, the decision boundary is able to be arranged at a position away from the centroid position of the pulmonary nodule region by a fixed distance on the basis of the known size of the pulmonary nodule.

Through the foregoing processing, the setting unit 1040 acquires information for setting the decision boundary. Finally, the setting unit 1040 sets the decision boundary in the composite masked image $M^{composite1}$. Specifically, a sphere with the center position $G^{nodule}$ and the radius $R^{decision}_{[k']}$ is drawn in the composite masked image $M^{composite1}$. A simplest method is to give pixel values representing pixels belonging to the decision boundary to all pixels at positions away from a pixel $G^{nodule}$ of the composite masked image $M^{composite1}$ by a distance r. Here, $R^{decision}_{[k']}<=r<=R^{decision}_{[k']}+\Delta R$ and $\Delta R>=0$. The pixel values may be any values as long as the decision boundary is able to be discriminated from the pulmonary nodule region $V^{nodule}$ or the candidate region $V^{candidate}_{[i]}$ in the composite masked image $M^{composite1}$. The closed curve 1660 drawn in the composite masked image 1600 of FIG. 6 is the decision boundary.

A value of $\Delta R$ may be any value as long as being 0 or more, but is desired to be a value by which a thickness (thickness of the closed curve 1660 of FIG. 6) of a spherical surface representing the decision boundary is at least two pixels or more or pixels representing the decision boundary form combining of six pixels which are adjacent to each other. This is because an image treated by the image processing apparatus 100 according to the present embodiment is represented by a set of discrete pixels. In a case where 0 or a very small value is used for the value of $\Delta R$, the pixels representing the decision boundary may form combining of twenty-six pixels which are adjacent to each other. The decision boundary is not one closed curve but a plurality of line segments that are not combined with each other in some cases. In a case where such a decision boundary is set to the composite masked image $M^{composite1}$, processing of step S1060 described below may not exert an intended effect. Therefore, a value that is large to some extent may be given to $\Delta R$. For example, the value of $\Delta R$ may be 10% of the value of $R^{decision}_{[k']}$ ($\Delta R=0.1 \times R^{decision}_{[k']}$). Additionally, the value of $\Delta R$ may be set so that all pixels at positions away from the pixel $G^{nodule}$ by $R^{decision}_{[k']}$ or more among the pixels of the composite masked image $M^{composite1}$ represent the decision boundary. Due to characteristics of the processing of step S1060, there is no problem with use of a large value as the value of $\Delta R$.

After finishing all the processing described above, the setting unit 1040 saves the composite masked image $M^{composite1}$ in the storage unit 120.

This is the end of the description for the processing performed by the setting unit 1040 at step S1060.

Now, a method of establishing the list $L_1$ stored in the data server 130 will be described. The sets ($R^{nodule}_{[k]}$, $R^{decision}_{[k]}$) of values stored in the list $L_1$ are determined, for example, from a plurality of learning images collected in advance.

First, a user measures a radius of a pulmonary nodule region that exists in each of the learning images. Next, the user classifies the learning images in accordance with radiuses of pulmonary nodule regions. For example, a learning image in which a pulmonary nodule whose radius is less than 5 mm is drawn is classified as a group 1. Then, a learning image in which a pulmonary nodule whose radius is 5 mm or more and less than 10 mm is drawn is classified as a group 2. In this manner, all the learning images are classified as any groups that are defined in 5 mm increments of the radius. Note that, the measurement of the radius of the pulmonary nodule region and the classification of the learning images may be performed by the image processing apparatus 100.

Note that, though the learning images are classified as any groups that are defined in 5 mm increments, such a method is merely an example and the learning images may be classified as groups by another method. That is, the number of groups for the classification is not limited to two and may be three or more, and the groups may not be defined in 5 mm increments. A size of the increment for the classification of the learning images may be determined in accordance with extraction accuracy of a desired bronchus region in processing for determining a radius of a decision boundary described below.

After classifying all the leaning images on the basis of the radiuses of the pulmonary nodule regions, the image processing apparatus 100 acquires a value of the radius of the decision boundary by which a desired bronchus region is extracted with the highest accuracy in each of the groups. At the present step, the image processing apparatus 100 selects one value in a range of [$R^{decision}_{min}$, $R^{decision}_{max}$] ($R^{decision}_{min}$ and $R^{decision}_{max}$ will be described below). Then, the processing from steps S1010 to S1070 performed by the image processing apparatus 100 according to the first embodiment is applied to each of the learning images, a desired region is actually extracted, and extraction accuracy is calculated. At this time, the image processing apparatus 100 uses the previously selected value as a temporary radius of the decision boundary. Such sequential processing is performed with various values in the range [$R^{decision}_{min}$, $R^{decision}_{max}$] and the image processing apparatus 100 obtains extraction accuracy for each of the values. In this manner, a relationship between the radius of the decision boundary and the extraction accuracy for each of the groups of the learning images is able to be acquired. Finally, the image processing apparatus 100 selects the radius of the decision boundary by which the highest extraction accuracy is achieved in each of the groups of the learning images, as the radius $R^{decision}_{[k]}$ of the decision boundary in the group. Note that, the extraction accuracy is able to be obtained by, for example, a matching degree between correct data of the pulmonary nodule region that is determined in advance and an extraction result of the image processing apparatus 100.

Here, $R^{decision}_{min}$ and $R^{decision}_{max}$ used in the processing described above will be described. It may be set that $R^{decision}_{min}$ is an average radius value $R^{nodule}$ of a pulmonary nodule region drawn in a learning image to be processed. On the other hand, it may be set that $R^{decision}_{max}$ is a distance from the pulmonary nodule region drawn in the learning image to be processed to a trachea region.

After the radius $R^{decision}_{[k]}$ of the decision boundary by which the highest extraction accuracy is achieved in each of the groups is obtained, the radius $R^{decision}_{[k]}$ of the decision boundary and a representative value of the radius of the pulmonary nodule region belonging to the group are set as a set of values. Here, the representative value of the radius of the pulmonary nodule region may be a median value of radiuses of pulmonary nodule regions belonging to each of the groups, for example. For example, in the case of the pulmonary nodule (pulmonary nodule with 5 mm or more and less than 10 mm) of the group 2, $R^{nodule}_{[2]}$=7.5 mm. The representative value $R^{nodule}_{[k]}$ of the radius of the pulmonary nodule region and the radius $R^{decision}_{[k]}$ of the decision boundary that are obtained as described above are stored in order as one set of values ($R^{nodule}_{[k]}$, $R^{decision}_{[k]}$) in the data server 130. Finally, it is to be noted that the processing for determining the radius of the decision boundary described here may be performed once at a stage where the image processing apparatus 100 according to the first embodiment is established and does not need to be performed at a stage where the original image is processed.

This is the end of the description for the method of establishing the list $L_1$ stored in the data server 130. (S1070)

Figure 7:
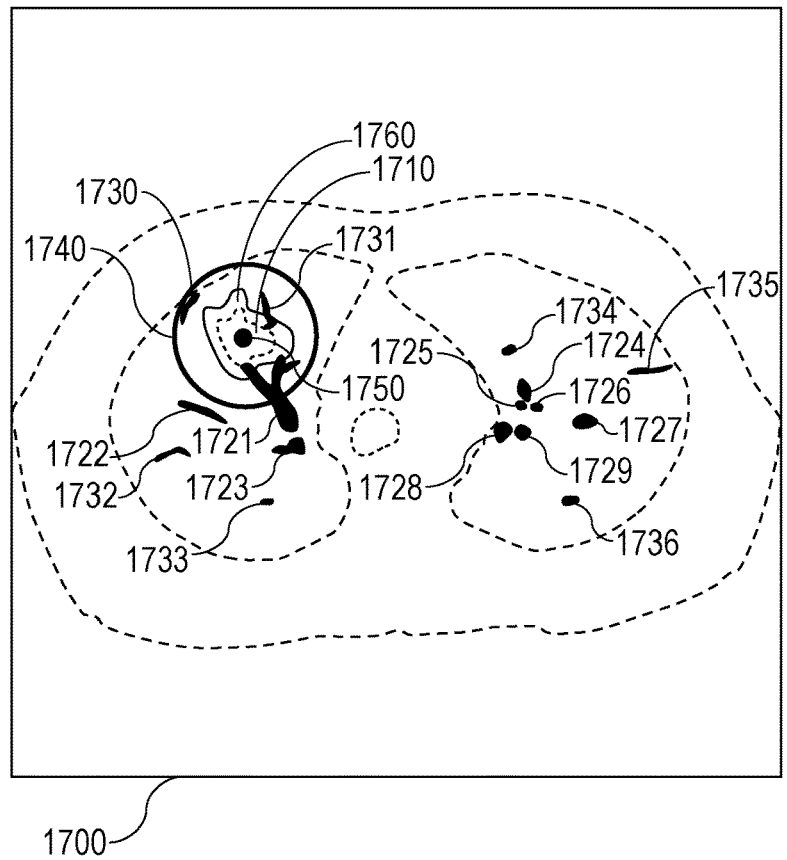
FIG. 7 is a schematic view for explaining an example of decision processing performed by the image processing apparatus according to the first embodiment.

At step S1070, the decision unit 1050 decides whether or not each of the candidate regions in the composite masked image is a desired region. With reference to FIG. 7, processing of the decision unit 1050 will be described. An image 1700 of FIG. 7 is a composite masked image $M^{composite1}$. A region 1710 surrounded by a broken line in the composite masked image 1700 is a pulmonary nodule region $V^{nodule}$. Regions 1721 to 1736 are candidate regions $V^{candidate}_{[i]}$.

First, the decision unit 1050 acquires the composite masked image $M^{composite1}$ from the storage unit 120.

Next, the decision unit 1050 applies a dilation operation that is one of morphological operations for the pulmonary nodule region $V^{nodule}$ in the composite masked image $M^{composite1}$. Then, the decision unit 1050 acquires an extension region $V^{nodule'}$ of the pulmonary nodule region $V^{nodule}$. Note that, the dilation operation is not essential processing. Here, the pulmonary nodule region $V^{nodule}$ and the extension region $V^{nodule'}$ correspond to an example of a region related to the pulmonary nodule region.

For a structural element of the dilation operation, a sphere with the radius $R^{dilation1}$ is used. For a value of the radius $R^{dilation1}$, a value by which a desired bronchus region is able to be obtained with the highest accuracy when a bronchus region is extracted by actually applying the processing from steps S1010 to S1080 to a learning image of the same type as that of the original image is used. Note that, the radius $R^{dilation1}$ may have a value by which a desired bronchus region is able to be extracted with the accuracy of a given threshold or more when a bronchus region is extracted by actually applying the processing from steps S1010 to S1080 to a learning image of the same type as that of the image.

The value of $R^{dilation1}$ may be determined in accordance with the average radius $R^{nodule}$ of the pulmonary nodule region. In this case, $R^{dilation1}$ may be determined by using a method similar to the method of determining the radius $R^{decision}_{[k]}$ of the decision boundary in accordance with the average radius $R^{nodule}$ of the nodule. The description for step S1060 is to be referred to for specific processing.

In the image 1700 of FIG. 7, a region 1760 surrounded by a solid line is the extension region $V^{nodule'}$. The extension region 1760 is a region obtained by extending the pulmonary nodule region 1710 with a centroid 1750 as the center.

After acquiring the extension region $V^{nodule'}$, the decision unit 1050 decides whether or not each of the candidate regions $V^{candidate}_{[i]}$ (1<=<=$N^{candidate}$) in the composite masked image $M^{composite1}$ is a desired region. Here, the decision means, for example, processing for checking that at least $N^{voxel}$ pixel among pixels belonging to the candidate region $V^{candidate}_{[i]}$ contacts or overlaps with both the extension region $V^{nodule'}$ and the decision boundary $V^{decision}$. Here, a value by which a desired bronchus region is able to be obtained with the highest accuracy when a bronchus region is extracted by actually applying the processing from steps S1010 to S1080 to a learning image of the same type as that of the original image is used for $N^{voxel}$. Note that, $N^{voxel}$ may have a value of the decision boundary by which a desired bronchus region is able to be extracted with the accuracy of a given threshold or more when a bronchus region is extracted by actually applying the processing from steps S1010 to S1080 for a learning image of the same type as that of the original image. That is, $N^{voxel}$ may have any value and may be, for example, one pixel or more.

In a case where the candidate region $V^{candidate}_{[i]}$ contacts or overlaps with the extension region $V^{nodule'}$ and the decision boundary $V^{decision}$, the decision unit 1050 stores a decision result "true" in a variable $B_{[i]}$ that stores the decision result. To the contrary, in a case where the candidate region $V^{candidate}_{[i]}$ contacts with only any of the extension region $V^{nodule'}$ and the decision boundary $V^{decision}$, the decision unit 1050 stores a decision result "false" in the variable $B_{[i]}$. After making decision for all the candidate regions $V^{candidate}_{[i]}$ the decision unit 1050 saves a decision result $B_{[i]}$ in the storage unit 120. Note that, in a case where the dilation processing is not performed, the decision unit 1050 decides whether the pulmonary nodule region $V^{nodule}$ instead of the extension region $V^{nodule'}$ contacts or overlaps with the candidate region $V^{candidate}_{[i]}$.

Here, the decision results for the candidate regions 1721 to 1736 are checked. Since the candidate region 1721 contacts (overlaps) with both the extension region 1760 and the decision boundary 1740, the decision result is "true". Since the candidate region 1730 contacts (overlaps) with the decision boundary 1740 but does not contact (overlap) with the extension region 1760, the decision result is "false". To the contrary, since the candidate region 1731 contacts (overlaps) with the extension region 1760 but does not contact (overlap) with the decision boundary 1740, the decision result is "false". Since the candidate regions 1722 to 1729 and the candidate regions 1732 to 1736 contact (overlap) with neither the extension region 1760 nor the decision boundary 1740, the decision results are "false".

(S1080)

At step S1080, the acquisition unit 1060 acquires a desired bronchus region from among the candidate regions on the basis of the results of the decision performed at step S1070. Here, the desired bronchus is, for example, a bronchus running around a target pulmonary nodule and it may be said that the desired bronchus is a bronchus running from the trachea to the nodule from a different point of view.

First, the acquisition unit 1060 acquires the composite masked image $M^{composite1}$ and all the decision results $B_{[i]}$ ($1<=i<=N^{candidate}$) from the storage unit 120. Next, the acquisition unit 1060 generates a masked image (bronchus masked image $M^{bronchus}$) with the same image size as that of the composite masked image $M^{composite1}$. Pixel values representing a non-bronchus pixel are substituted for all pixels of the bronchus masked image $M^{bronchus}$.

After generating the bronchus masked image $M^{bronchus}$, the acquisition unit 1060 checks the decision result $B_{[i]}$ for each of the candidate regions $V^{candidate}_{[i]}$ in the composite masked image. When the decision result $B_{[i]}$ is "true", the acquisition unit 1060 acquires the candidate region $V^{candidate}_{[i]}$ as the desired region $V^{bronchus}$. Then, the acquisition unit 1060 sets pixel values of pixels corresponding to pixels that belong to the acquired region in the bronchus masked image $M^{bronchus}$ as "bronchus pixels". By applying such processing to all the candidate regions $V^{candidate}_{[i]}$, the acquisition unit 1060 acquires a desired region.

Figure 8:
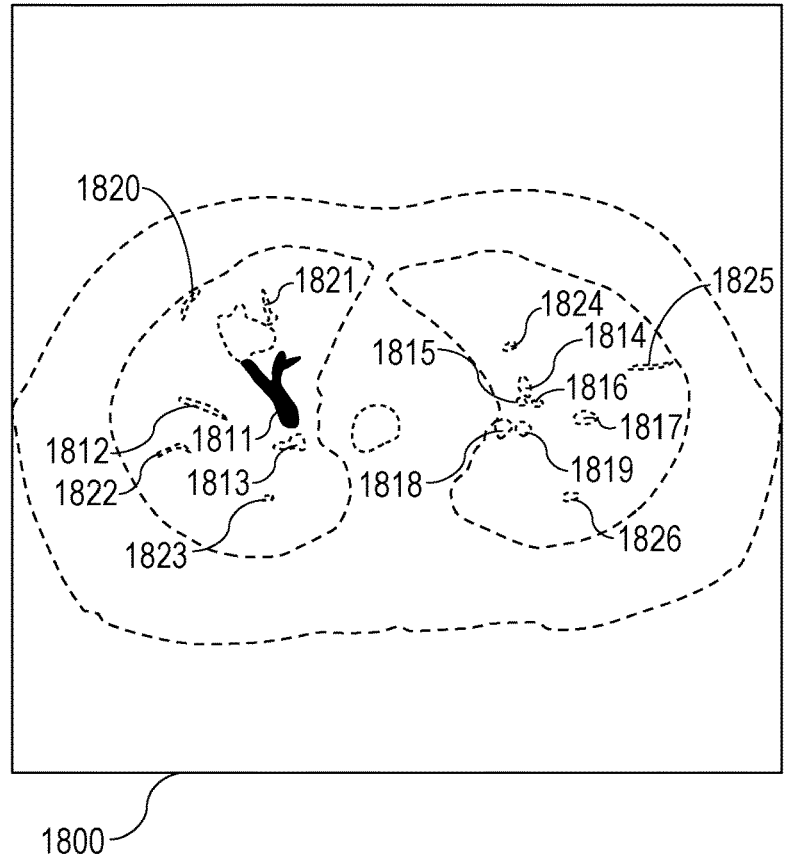
FIG. 8 is a schematic view for explaining an example of a desired bronchus region acquired by the image processing apparatus according to the first embodiment.

FIG. 8 illustrates an example of the bronchus masked image acquired at the present step. A bronchus masked image 1800 of FIG. 8 is obtained as a result of applying the acquisition processing of the present step to the candidate regions 1721 to 1736 in the composite masked image 1700 of FIG. 7. According to the processing of step S1070, the decision result for only the candidate region 1721 of FIG. 7 is "true" and the decision results for the other candidate regions are "false". On the basis of the decision results, the region 1721 is acquired as a desired region 1811 in the present step. The candidate regions (candidate regions 1722 to 1736) other than the candidate region 1721 are not acquired.

The bronchus masked image $M^{bronchus}$ generated by the acquisition unit 1060 is saved in the data server 130 via the storage unit 120.

In accordance with the foregoing procedure, the image processing apparatus 100 according to the first embodiment performs processing for extracting the bronchus running around the target pulmonary nodule.

Now, processing for extracting an artery and vein running around and toward the target pulmonary nodule by the image processing apparatus 100 according to the first embodiment will be described. In the processing performed by the image processing apparatus 100 according to the first embodiment, the processing of steps S1010, S1020, and S1030 is performed in the same manner also in the extraction of an artery and vein region. At step S1040, the second extraction unit 1020 extracts not the bronchus region but candidate regions of the artery and vein. The artery and vein region forms a thin tubular structure (inside of which forms a thick linear structure) similarly to the bronchus region. On the other hand, differently from the bronchus region, the artery and vein region has a CT value higher than that of the lung field region. Thus, at step S1040, the second extraction unit 1020 applies threshold processing ($I^{input}(p)>T^{input}_1$ and $L^{line}(p)>T^{line}$) to the original image and $L^{line}(p)$ calculated for each pixel of the original image, and thereby acquires a pixel that is likely to belong to the artery and vein region in the original image. Then, the second extraction unit 1020 performs region extension processing by using an extension condition "a pixel value $I^{input}(p')$ of a pixel p' within a radius$^{RG}_1$ with an extension candidate pixel p as the center is larger than a threshold $T^{input}_2$ ($I^{input}(p')>T^{input}_2$)". At steps S1050, S1060, S1070, and S1080, similar processing to the processing in the extraction of the bronchus region may be performed.

In accordance with the foregoing procedure, the image processing apparatus 100 according to the first embodiment performs processing for extracting the artery and vein running around the target pulmonary nodule.

The image processing apparatus 100 according to the first embodiment is able to extract a region of a structure (bronchus or artery and vein) running around the target pulmonary nodule by the processing described above with higher accuracy than conventional one. That is, a bronchus or an artery and vein that is related to the target pulmonary nodule among bronchi or arteries and veins is able to be extracted with high accuracy. In other words, a bronchus or an artery and vein that is likely to be particularly focused on by a doctor among bronchi or arteries and veins is able to be extracted with high accuracy.

Second Embodiment

An image processing apparatus according to a second embodiment cuts out a part of an original image and generates a partial image. Then, the image processing apparatus sets a decision boundary to an edge of the generated partial image. Here, the partial image is cut out so as to include a pulmonary nodule region drawn in an original image. An image size of the partial image is determined on the basis of an average radius of the pulmonary nodule region drawn in the original image. As a result, the decision boundary is set at a position away from the pulmonary nodule region by a distance that is determined on the basis of the average radius of the pulmonary nodule region. The image processing apparatus according to the second embodiment will be described below.

Figure 9:
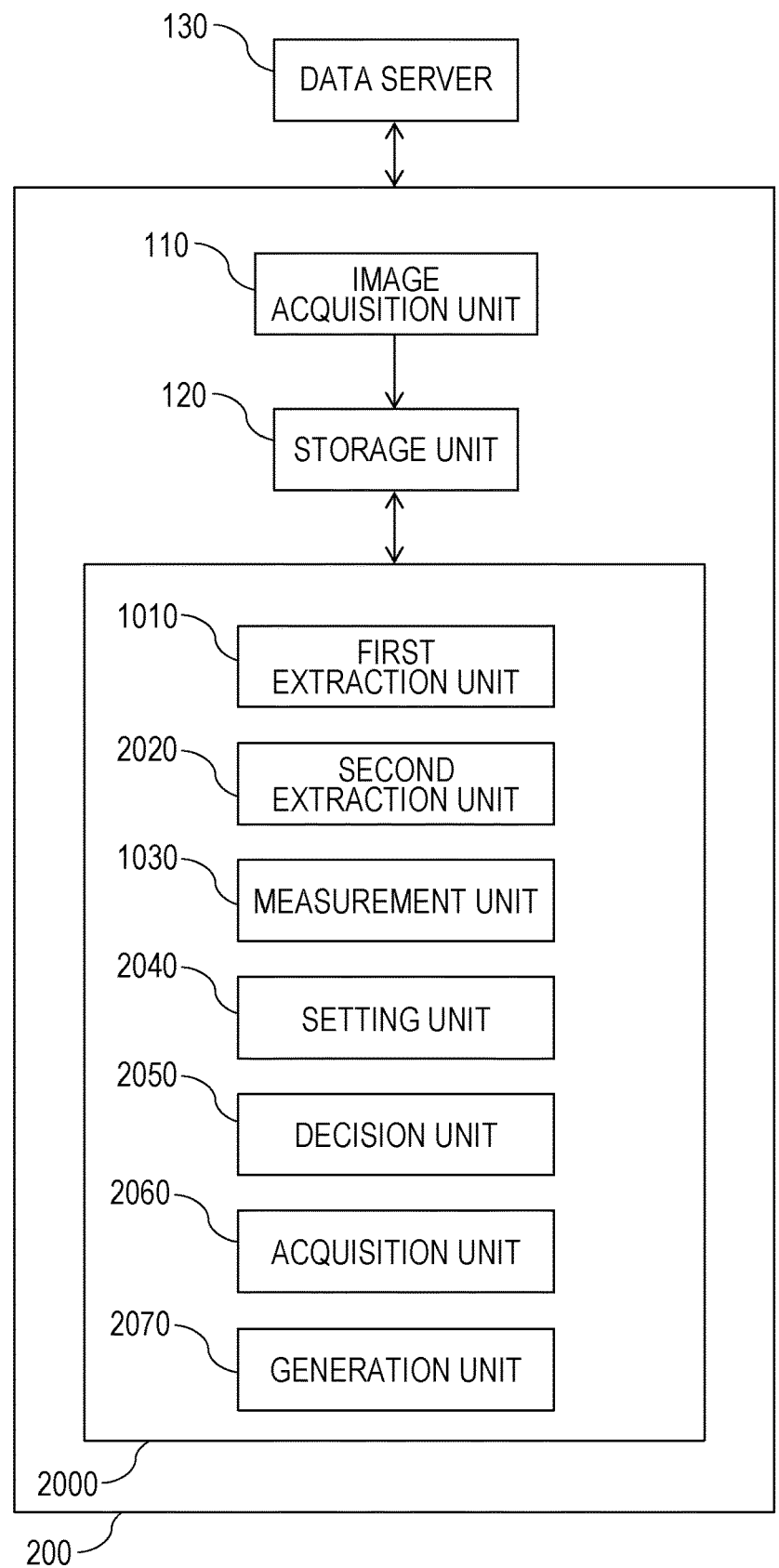
FIG. 9 illustrates an example of a functional configuration of the image processing apparatus according to the second embodiment.

A functional configuration of the image processing apparatus according to the present embodiment will be described with reference to FIG. 9. An image processing unit 2000 of an image processing apparatus 200 according to the second embodiment includes a first extraction unit 1010, a second extraction unit 2020, a measurement unit 1030, a setting unit 2040, a decision unit 2050, an acquisition unit 2060, and a generation unit 2070. Similarly to the first embodiment, functions of the aforementioned units are realized by one or more processors included in the image processing apparatus 200. Among the processing units, the first extraction unit 1010 and the measurement unit 1030 perform the same processing as the processing units in the image processing apparatus 100 according to the first embodiment. Thus, description for the processing units will be omitted.

The second extraction unit 2020, the decision unit 2050, and the acquisition unit 2060 perform equivalent processing to that of the second extraction unit 1020, the decision unit 1050, and the acquisition unit 1060 in the image processing apparatus 100 according to the first embodiment. However, the second extraction unit 2020, the decision unit 2050, and the acquisition unit 2060 perform processing for the partial image and a partial composite masked image.

The setting unit 2040 generates a composite masked image from a partial pulmonary nodule masked image and a partial candidate masked image described below. Then, the setting unit 2040 sets a decision boundary to an edge of the generated composite masked image. The generated composite masked image is saved in the storage unit 120.

The generation unit 2070 performs two kinds of image size changing processing. The first image size changing processing is cutting out of an image. After the first extraction unit 1010 and the measurement unit 1030 finish processing, the generation unit 2070 acquires an original image, a pulmonary nodule masked image, and a coordinate value of a centroid position of a pulmonary nodule region from the storage unit 120. Then, the generation unit 2070 cuts out parts of the original image and the pulmonary nodule masked image and generates the cut-out parts as new images. A cut-out range of each of the images is set as a range surrounded by a rectangle which is almost centered around a position of the same coordinate in each of the images as that of the centroid position of the pulmonary nodule region and has a size determined by a predetermined method. Note that, the shape of the cut-out range is not limited to the rectangle. Through the cut-out processing, a partial image is generated from the original image. Similarly, a partial pulmonary nodule masked image is generated from the pulmonary nodule masked image. The two images are saved in the storage unit 120.

The second image size changing processing performed by the generation unit 2070 is processing for changing an image size of a masked image (partial bronchus masked image) generated by the acquisition unit 2060 to the same image size as that of the original image. Though details will be described below, the image processing apparatus 200 according to the second embodiment extracts a bronchus region existing in the partial image. Since the partial image is an image cut out from the original image, the image size of the partial bronchus masked image is different from that of the original image. Thus, the generation unit 2070 changes the image size of the partial bronchus masked image so that the image size of the partial bronchus masked image is the same as the image size of the original image. It is to be noted that such processing is processing performed by procedure reverse to that of the first image size changing processing.

Figure 10:
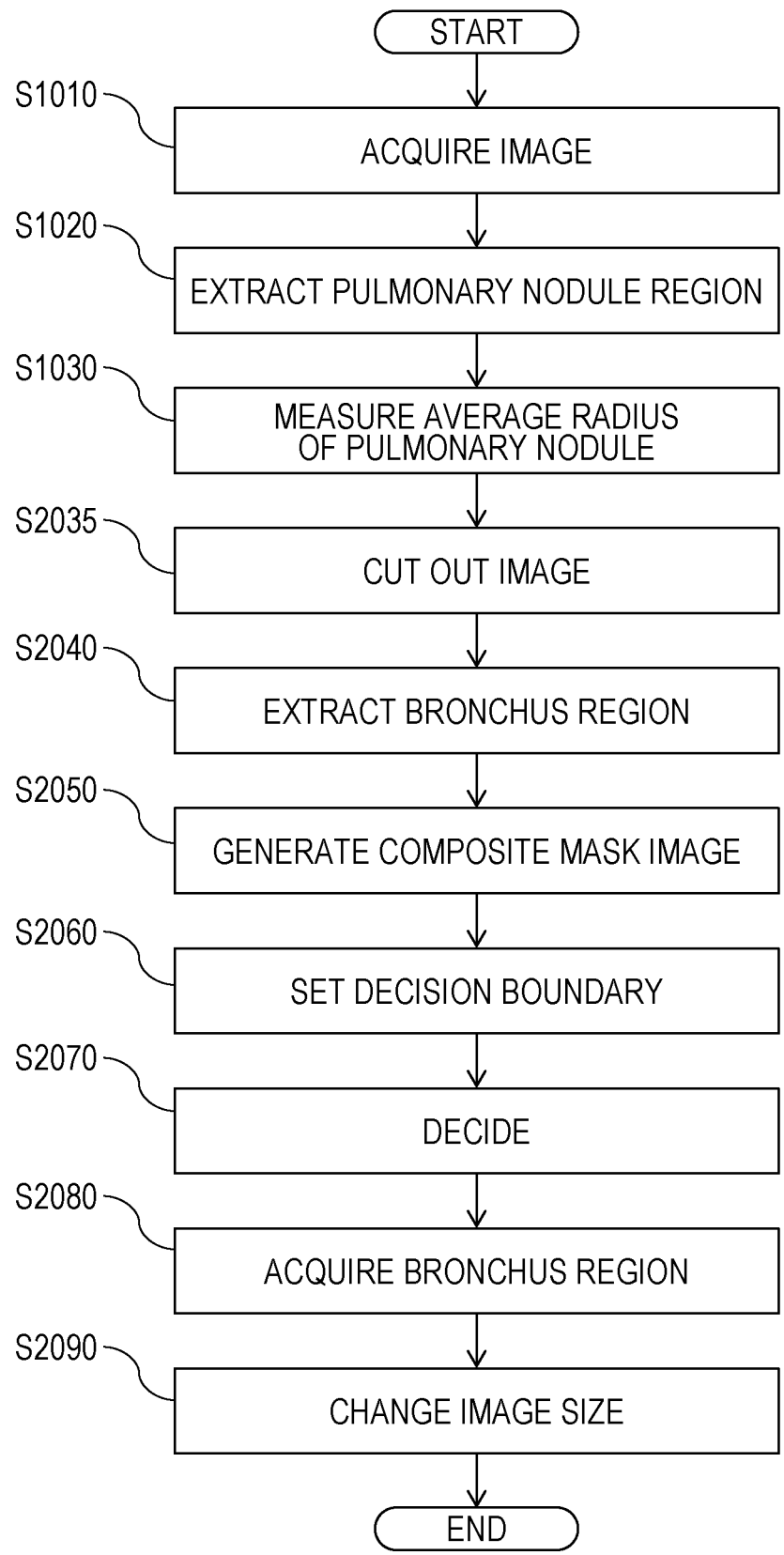
FIG. 10 is a flowchart illustrating an example of processing procedure of the image processing apparatus according to the second embodiment.

Next, processing procedure of the image processing apparatus 200 of the present embodiment will be described with reference to FIG. 10. The image processing apparatus 200 according to the present embodiment performs the processing of steps S1010, S1020, and S1030 executed by the image processing apparatus 100 according to the first embodiment. Then, the image processing apparatus 200 performs processing of steps S2035, S2040, S2050, S2060, S2070, S2080, and S2090 described below.

(S2035)

At step S2035, the generation unit 2070 acquires the original image and the pulmonary nodule masked image from the storage unit 120. Then, from each of the images, the generation unit 2070 cuts out a predetermined range (cut-out range) in the image and generates a partial image and a partial pulmonary nodule masked image. Note that, since the original image is a three-dimensional image, the cut-out range referred to herein is a rectangular parallelepiped region. Each image generated at the present step is a three-dimensional image. When the original image is a two-dimensional image, the cut-out range is a rectangular region and the generated image is a two-dimensional image. Note that, the rectangular parallelepiped region and the rectangular region respectively include a cubic region and a square region.

Figure 11:
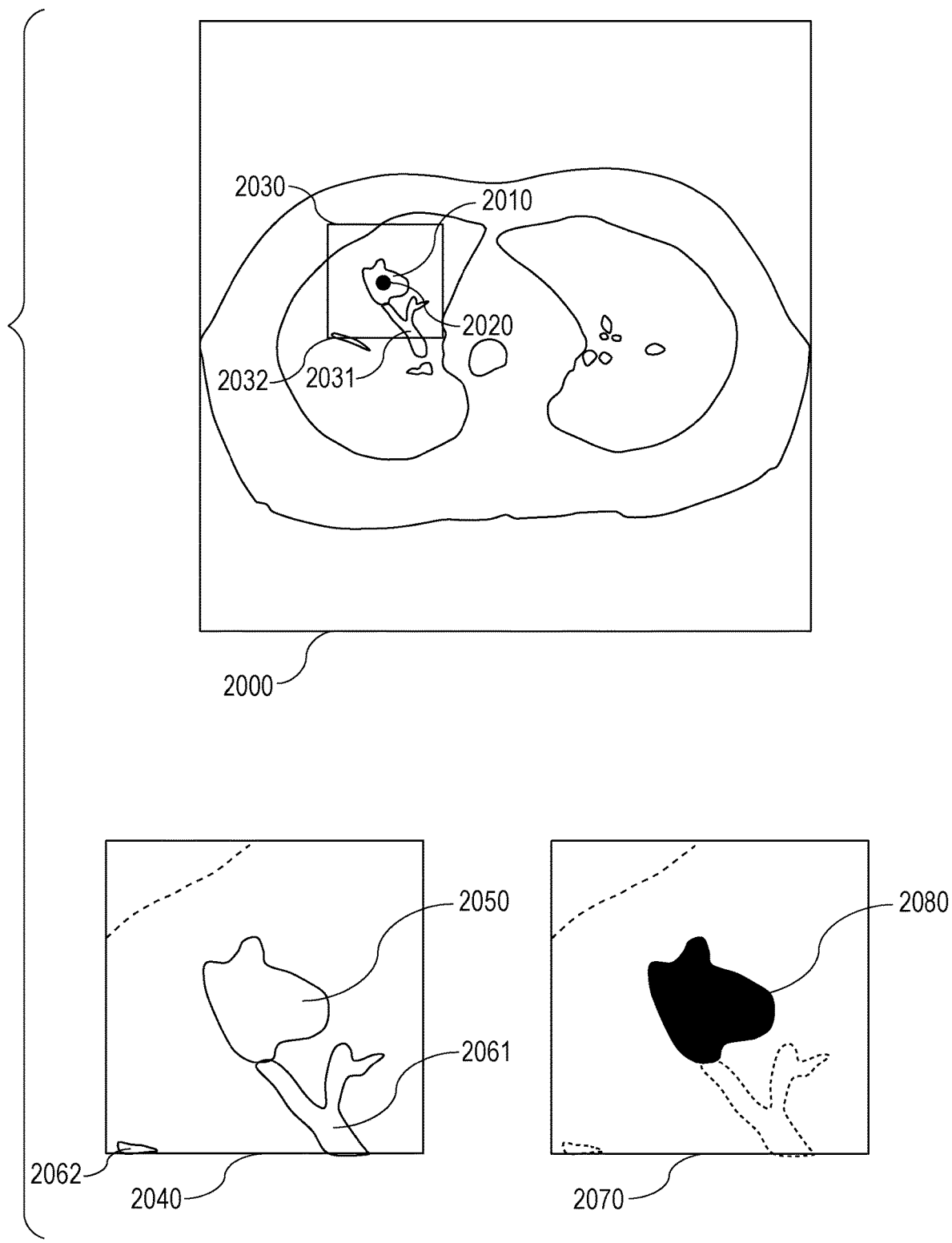
FIG. 11 is a schematic view illustrating an example of generation of a partial image and a partial pulmonary nodule masked image.

The generation of the partial image and the partial pulmonary nodule masked image will be described with reference to FIG. 11. An image 2000 of FIG. 11 is the original image processed by the image processing apparatus 200 according to the second embodiment. This image is the same image as the original image 1300 of FIG. 3.

First, the generation unit 2070 determines a center position of a cut-out range. Here, the center position of the cut-out range is set as a centroid position of the pulmonary nodule region. The coordinate value $G^{nodule}$ of the centroid position of the pulmonary nodule region has been already calculated at step S1030 and saved in the storage unit 120. Thus, the generation unit 2070 acquires the coordinate value $G^{nodule}$ of the centroid position of the pulmonary nodule region from the storage unit 120. Then, the acquired value is used as the coordinate value of the center of the decision boundary. A black point 2020 in the image 2000 of FIG. 11 is the coordinate value $G^{nodule}$ of the centroid position of the pulmonary nodule region.

Next, the generation unit 2070 determines a size of the cut-out range. Here, the size of the cut-out range is defined by a length ($W^{voi} \times H^{voi} \times D^{voi}$) of one side of the rectangular parallelepiped region. Here, $W^{voi}$, $H^{voi}$, and $D^{voi}$ are positive integers. The length ($W^{voi} \times H^{voi} \times D^{voi}$) of one side of the rectangular parallelepiped region is set to be twice as long as a radius of a decision boundary optimum for extraction of a desired bronchus region from the original image. A specific determination method conforms to a method of determining the radius of the decision boundary at step S1060 by the setting unit 1040 of the image processing apparatus 100 according to the first embodiment. Details thereof will be described below.

An average radius of the pulmonary nodule region is required to determine the radius of the decision boundary and the average radius $R^{nodule}$ of the pulmonary nodule region has been already measured at step S1030 and saved in the storage unit 120. Thus, the generation unit 2070 acquires the average radius $R^{nodule}$ of the pulmonary nodule region from the storage unit 120. Then, the generation unit 2070 acquires, from the storage unit 120, a list $L_1$ to determine the radius of the decision boundary. Details of the values stored in the list $L_1$ are as described in the explanation for the first embodiment. After acquiring the average radius $R^{nodule}$ of the pulmonary nodule region and the list $L_1$, the generation unit 2070 determines the radius of the decision boundary. A method of determining the radius of the decision boundary is also as described in the explanation for step S1060. Through the foregoing processing, the generation unit 2070 obtains a radius $R^{decision}_{[k']}$ of the decision boundary. Finally, the generation unit 2070 sets the size of the cut-out range to be twice ($W^{voi}=H^{voi}=D^{voi}=2\times R^{decision}_{[k']}$) as long as the radius $R^{decision}_{[k']}$ of the decision boundary. Note that, a coefficient to be multiplied by the radius $R^{decision}_{[k']}$ of the decision boundary is not limited to 2.

Note that, there is a case where the average radius of the pulmonary nodule region drawn in the original image is known by some method before the image processing apparatus 200 of the present embodiment starts processing. An example thereof includes a case where the operator limits a size of the pulmonary nodule to be processed by the image processing apparatus 200 of the present embodiment to a constant size in advance. In such a case, the generation unit 2070 may set a size ($W^{voi}_{const}$, $H^{voi}_{const}$, $D^{voi}_{const}$) of the cut-out range that is determined in advance as the size of the cut-out range of the original image. Here, the size ($W^{voi}_{const}$, $H^{voi}_{const}$, $D^{voi}_{const}$) of the cut-out range is a value determined on the basis of a known average radius $R^{nodule}_{known}$ of the pulmonary nodule drawn in the original image and may be set as to be twice as long as the average radius $R^{nodule}_{known}$ for example. Note that, in a case where the average radius of the pulmonary nodule region drawn in the original image is known in advance by some method, the generation unit 2070 does not need to acquire the list $L_1$ from the storage unit 120. As described above, also in a case where the size of the pulmonary nodule is known, the decision boundary is able to be arranged at a position away from the centroid position of the pulmonary nodule region by a fixed distance on the basis of the known size of the pulmonary nodule.

A rectangle 2030 in the image 2000 of FIG. 11 is the cut-out range determined in the present step. It is found that the center of the cut-out range 2030 matches the centroid position 2020 of the pulmonary nodule region.

After determining the center position $G^{nodule}$ and the size ($W^{voi} \times H^{voi} \times D^{voi}$) of the cut-out range, the generation unit 2070 cuts out images in the cut-out range determined by the aforementioned method from the original image and the pulmonary nodule masked image. The cut-out images are set as a partial image $I^{voi}$ and a partial pulmonary nodule masked image $M^{nodule}$. The partial image $I^{voi}$ and the partial pulmonary nodule masked image $M^{nodule}$ that are generated are saved in the storage unit 120.

An image 2040 of FIG. 11 is the partial image cut out from the original image 2000. A pulmonary nodule 2050 of the partial image 2040 corresponds to a pulmonary nodule 2010 drawn in the original image 2000. A bronchus 2061 and a bronchus 2062 of the partial image 2040 respectively correspond to a bronchus 2031 and a bronchus 2032 of the original image 2000.

An image 2070 of FIG. 11 is a partial pulmonary nodule masked image $M^{nodule}$ cut out from the pulmonary nodule masked image (not illustrated). A region 2080 of the partial masked image pulmonary nodule masked image 2070 is a pulmonary nodule region $V^{nodule}$. The region has been extracted from the original image 2000 at step S1020.

(S2040)

At step S2040, the second extraction unit 2020 extracts candidate regions of the bronchus existing in the partial image. The processing of the present step is the same as the processing performed at step S1040 by the second extraction unit 1020 of the image processing apparatus 100 according to the first embodiment, but is different in that the candidate regions of the bronchus existing not in the original image but in the partial image are extracted. In the processing of the present step, a partial candidate masked image $M^{candidate}$ is generated. In the partial candidate masked image $M^{candidate}$, candidate regions $V^{candidate}_{[i]}$ exist.

(S2050)

At step S2050, the setting unit 2040 generates a composite masked image $M^{composite2}$. The processing of the present step is the same as the processing performed at step S1050 by the setting unit 1040 of the image processing apparatus 100 according to the first embodiment, but is different in that the composite masked image $M^{composite2 \; is}$ generated from the partial pulmonary nodule masked image $M^{nodule}$ and the partial candidate masked image $M^{candidate}$. A size of the composite masked image $M^{composite2}$ is smaller than a size of the composite masked image $M^{composite1}$ in the first embodiment.

(S2060)

At step S2060, the setting unit 2040 sets the decision boundary to an edge of the composite masked image $M^{composite2}$ With reference to FIG. 12, the decision boundary set at the present step will be described. An image 2100 of FIG. 12 is the composite masked image $M^{composite2}$. A region 2110 in the composite masked image 2100 is the pulmonary nodule region $V^{nodule}$. A region 2121, a region 2122, a region 2123, and a region 2124 are the candidate regions $V^{candidate}_{[i]}$ acquired at step S2040. Among the candidate regions, the candidate region 2121 and the candidate region 2124 are regions corresponding to the bronchus region 2031 and the bronchus region 2032 and it is found that the candidate regions 2121 and 2124 are extracted correctly. On the other hand, the candidate region 2122 and the candidate region 2123 are not bronchus regions, but are erroneously extracted as bronchus regions.

The setting unit 2040 sets the decision boundary to an edge of the composite masked image $M^{composite2}$. A region 2130, a region 2140, a region 2150, and a region 2160 that are indicated by diagonal lines in the composite masked image 2100 of FIG. 12 represent the decision boundary. As found from FIG. 12, the setting unit 2040 sets the decision boundary in the regions within a given range from the edge of the composite masked image 2100. The decision boundary needs to have a width of at least one pixel.

After setting the decision boundary, the setting unit 1040 saves the composite masked image $M^{composite2}$ in the storage unit 120.

(S2070)

At step S2070, the decision unit 2050 decides whether or not each of the candidate regions in the composite masked image is a desired region. The processing of the present step is the same as the processing performed at step S1070 by the decision unit 1050 of the image processing apparatus 100 according to the first embodiment. However, the decision processing is performed by referring to $M^{composite2}$.

Here, a result of the decision processing performed at the present step will be described with reference to an image 2200 of FIG. 13. The image 2200 is the composite masked image $M^{composite2}$. In the composite masked image 2200, a region 2270 surrounded by a solid line is an extension region $V^{nodule'}$. The extension region 2270 is a region obtained by dilating a pulmonary nodule region 2210, which is surrounded by a broken line, with a black point 2280 as the center. Note that, processing for dilating the pulmonary nodule region 2210 is not essential processing.

Since a candidate region 2221 contacts (overlaps) with both the extension region 2270 and a decision boundary 2260, the decision result is "true". Since a candidate region 2222 contacts (overlaps) with neither the extension region 2270 nor any decision boundary, the decision result is "false". Since a candidate region 2223 contacts (overlaps) with the extension region 2270 but does not contact (overlap) with the decision boundary, the decision result is "false". Since a candidate region 2224 contacts (overlaps) with the decision boundary 2260 but does not contact (overlap) with the extension region 2270, the decision result is "false".

(S2080)

At step S2080, the acquisition unit 2060 acquires a desired bronchus region from among the candidate regions on the basis of the results of decision performed at step S2070. The processing of the present step is the same as the processing performed at step S1080 by the acquisition unit 1060 of the image processing apparatus 100 according to the first embodiment. However, the processing for acquiring the bronchus region is performed by referring to $M^{composite2}$.

An image 2300 of FIG. 13 is the partial bronchus masked image $M^{bronchus}$ acquired in the present step. The partial bronchus masked image 2300 is obtained as a result of applying the acquisition processing of the present step to the composite masked image 2200. According to the processing of step S2070, the decision result for only the candidate region 2221 of the composite masked image 2200 is "true" and the decision results for the other candidate regions (the candidate region 2222, the candidate region 2223, and the candidate region 2224) are "false". On the basis of the decision results, the candidate region 2221 is acquired as a desired region 2311 in the present step. The candidate regions (the candidate region 2222, the candidate region 2223, and the candidate region 2224) other than the candidate region 2221 are not acquired.

(S2090)

At step S2090, the generation unit 2070 acquires the partial bronchus masked image from the storage unit 120. The generation unit 2070 changes an image size of the partial bronchus masked image to be the same as that of the original image.

It is assumed that the partial image is generated by cutting out a rectangular parallelepiped range with two points ($x_1$, $y_1$, $z_1$) and ($x_2$, $y_2$, $z_2$) in the original image as a diagonal line at step S2035. Here, $x_1$, $x_2$, $y_1$, $y_2$, $z_1$, and $z_2$ are positive integers that satisfy $1<=x_1<x_2<=W^{input}$, $1<=y_1<y_2<=H^{input}$, and $1<=z_1<z_2<=D^{input}$. Moreover, $W^{input}$, $H^{input}$, and $D^{input}$ are respectively pixel numbers in X, Y, and Z directions of the original image.

In the present step, the generation unit 2070 firstly generates a masked image with the same image size of $W^{input} \times H^{input} \times D^{input}$ as that of the original image. All pixel values of the masked image are set to be non-bronchus region pixels. Next, the generation unit 2070 copies pixel values of the partial bronchus masked image to a rectangular parallelepiped range with ($x_1$, $y_1$, $z_1$) and ($x_2$, $y_2$, $z_2$) in the masked image as a diagonal line. The generated masked image (bronchus masked image) is saved in the data server 130 via the storage unit 120.

In accordance with the foregoing procedure, the image processing apparatus 200 according to the second embodiment performs processing for extracting the bronchus running around the target pulmonary nodule.

Now, processing for extracting an artery and vein running around the target pulmonary nodule by the image processing apparatus 200 according to the second embodiment will be described. In the processing performed by the image processing apparatus 200 according to the second embodiment, the processing of steps S1010, S1020, S1030, and S2035 is performed in the same manner also in the extraction of an artery and vein region. At step S2040, the second extraction unit 2020 extracts not the bronchus region but candidate regions of the artery and vein. The processing for extracting the artery and vein region is as described in the explanation for the first embodiment. At steps S2050, S2060, S2070, S2080, and S2090, similar processing to the processing in the extraction of the bronchus region may be performed.

In accordance with the foregoing procedure, the image processing apparatus 200 according to the second embodiment performs processing for extracting the artery and vein running around the target pulmonary nodule.

The image processing apparatus 200 according to the second embodiment is able to extract a region of a structure (bronchus or artery and vein) running around the target pulmonary nodule by the processing described above with higher accuracy than conventional one. That is, a bronchus or an artery and vein that is related to the target pulmonary nodule among bronchi or arteries and veins is able to be extracted with high accuracy. In other words, a bronchus or an artery and vein that is likely to be particularly focused on by a doctor among bronchi or arteries and veins is able to be extracted with high accuracy. Additionally, according to the second embodiment, processing is performed for partially cut-out images, so that it is possible to extract a desired structure at a higher speed compared to the first embodiment. Since an edge of a cut-out range is set as a decision boundary, it is possible to decide a desired structure easily.

Third Embodiment

In the image processing apparatus according to the first or second embodiment, a decision boundary is represented by a closed surface that surrounds a pulmonary nodule region. Here, an essence of processing for extracting a structure region (bronchus or artery and vein region) by using the decision boundary is to set the decision boundary in a region where the structure runs. Meanwhile, a bronchus and a trachea have a tree structure. Thus, when a positional relation between a target pulmonary nodule and a trachea is known, a region where the bronchus related to the target pulmonary nodule runs is able to be estimated. Thus, in an image processing apparatus according to a third embodiment, the decision boundary is set in a region where the bronchus is expected to run on the basis of the positional relation between the pulmonary nodule and the trachea.

As to an artery and vein, when a positional relationship between the target pulmonary nodule and the artery and vein in mediastinum is known, a region where the artery and vein related to the target pulmonary nodule runs is able to be estimated. Thus, on the basis of the positional relationship between the pulmonary nodule and the artery and vein in the mediastinum, the decision boundary is set in a region where the artery and vein is expected to run in a lung field region.

The image processing apparatus according to the third embodiment will be described below.

Figure 14:
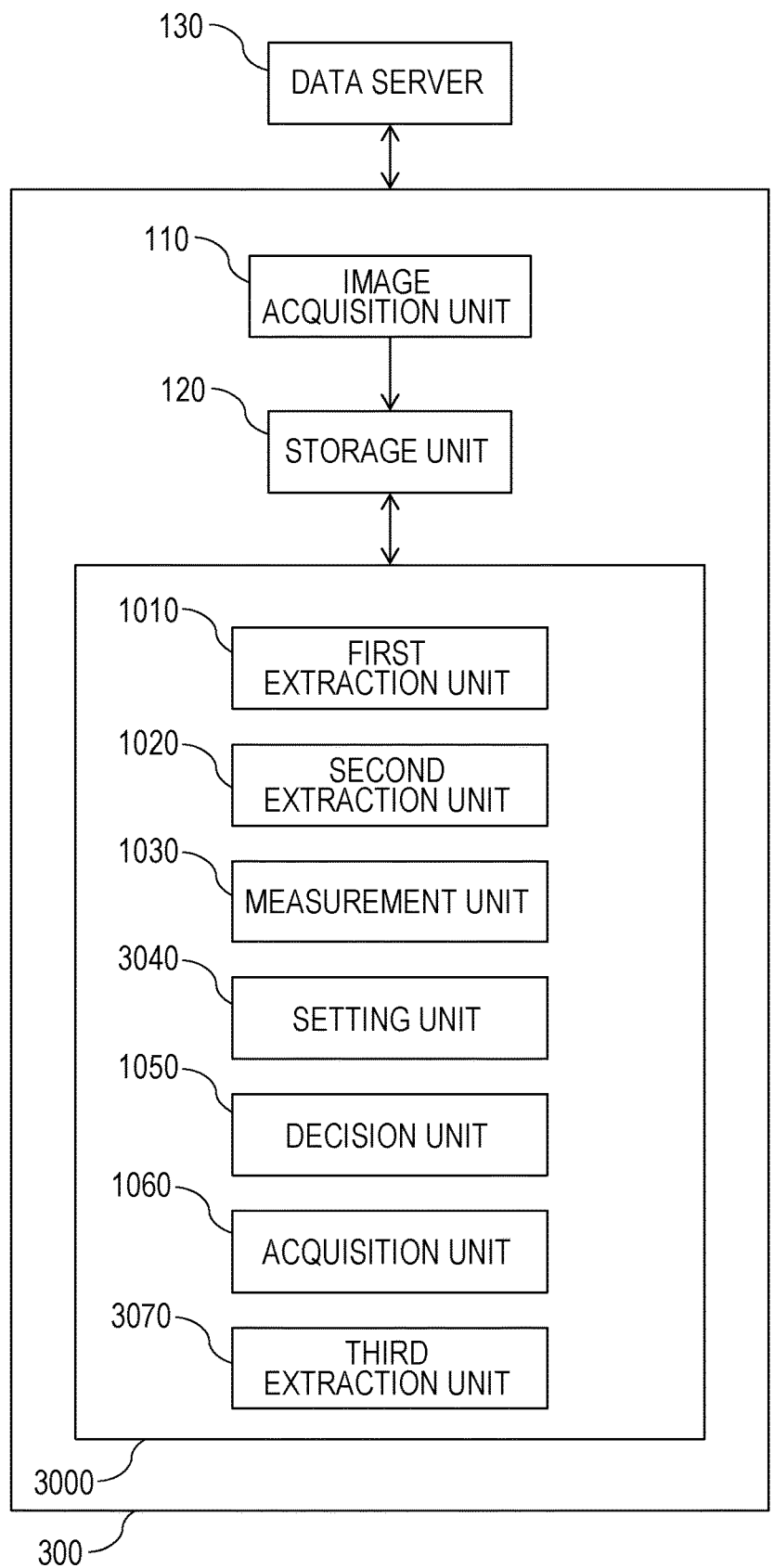
FIG. 14 illustrates an example of a functional configuration of an image processing apparatus according to a third embodiment.

A functional configuration of the image processing apparatus according to the present embodiment will be described with reference to FIG. 14. An image processing unit 3000 of an image processing apparatus 300 according to the third embodiment includes a first extraction unit 1010, a second extraction unit 1020, a measurement unit 1030, a setting unit 3040, a decision unit 1050, an acquisition unit 1060, and a third extraction unit 3070. Similarly to the first embodiment, functions of the aforementioned units are realized by one or more processors included in the image processing apparatus 300. Among the processing units, processing units other than the setting unit 3040 and the third extraction unit 3070 perform the same processing as the processing units in the image processing apparatus 100 according to the first embodiment. Thus, description for the processing units will be omitted.

The setting unit 3040 generates a composite masked image from a pulmonary nodule masked image, a candidate masked image, and a bronchus masked image. Next, the setting unit 3040 sets a decision boundary in the composite masked image on the basis of a positional relationship between a pulmonary nodule region extracted by the first extraction unit 1010 and a trachea region extracted by the third extraction unit 3070 described below. Finally, the setting unit 3040 saves the composite masked image in the storage unit 120.

The third extraction unit 3070 acquires an original image from the storage unit 120. Then, the third extraction unit 3070 applies a known image segmentation method to the original image and extracts a trachea region drawn in the original image. The third extraction unit 3070 acquires an extraction result in a format of a masked image (trachea masked image). The acquired trachea masked image is saved in the storage unit 120.

Figure 16:
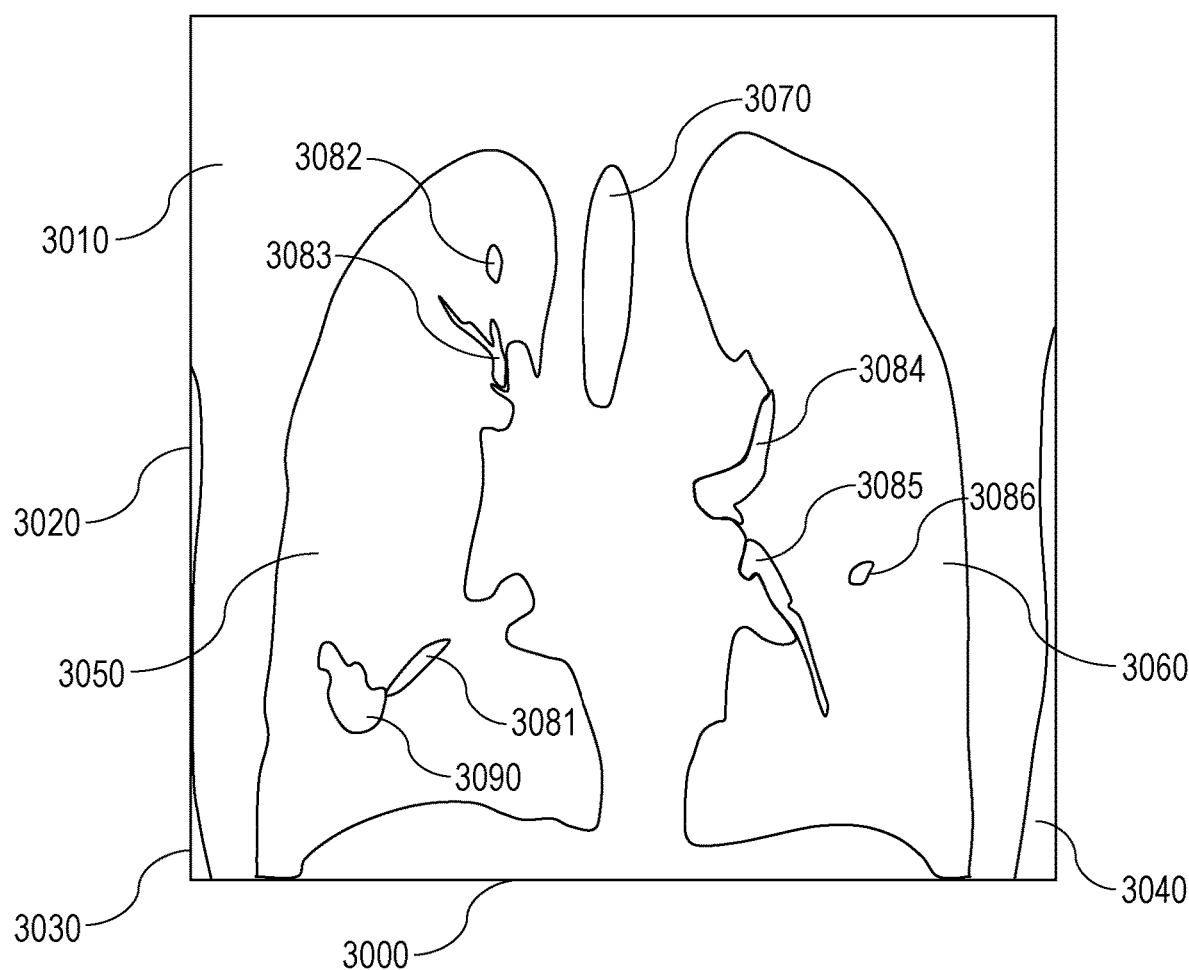
FIG. 16 is a schematic view illustrating an example of an original image processed by an image processing apparatus according to a third or fourth embodiment.

With reference to FIG. 16, the original image processed by the image processing apparatus 300 according to the present embodiment will be described. An image 3000 of FIG. 16 is one cross-sectional image of a plurality of cross-sectional (coronal cross-sectional) images that constitute a three-dimensional chest CT image (original image). Though FIG. 16 illustrates one representative cross-sectional image in the original image due to limitation of a drawing, the original image includes many cross-sectional images. Though FIG. 16 illustrates an example in which the original image is constituted by a coronal cross-sectional image for ease of understanding, the original image may be constituted by a different cross-sectional image (for example, an axial cross-sectional or a sagittal cross-sectional image).

A torso 3010 of a patient, an air region 3020, an air region 3030, and an air region 3040 around the torso are captured in the original image 3000. Further, a right lung 3050 and a left lung 3060 exist in the torso 3010. It is to be noted that, in the CT image, the right lung is captured on a right side of the image and the left lung is captured on a left side of the image. A trachea 3070 exists in the center of the torso 3010. Bronchi 3081 to 3086 exist in the right lung 3050 and the left lung 3060. The bronchi form a three-dimensional linear structure and are connected to the trachea 3070 by a tomographic image (not illustrated). A pulmonary nodule 3090 exists in the right lung 3050. In FIG. 16, a region of the bronchus 3081 is a bronchus region (desired bronchus region) that is desired to be extracted.

Figure 15:
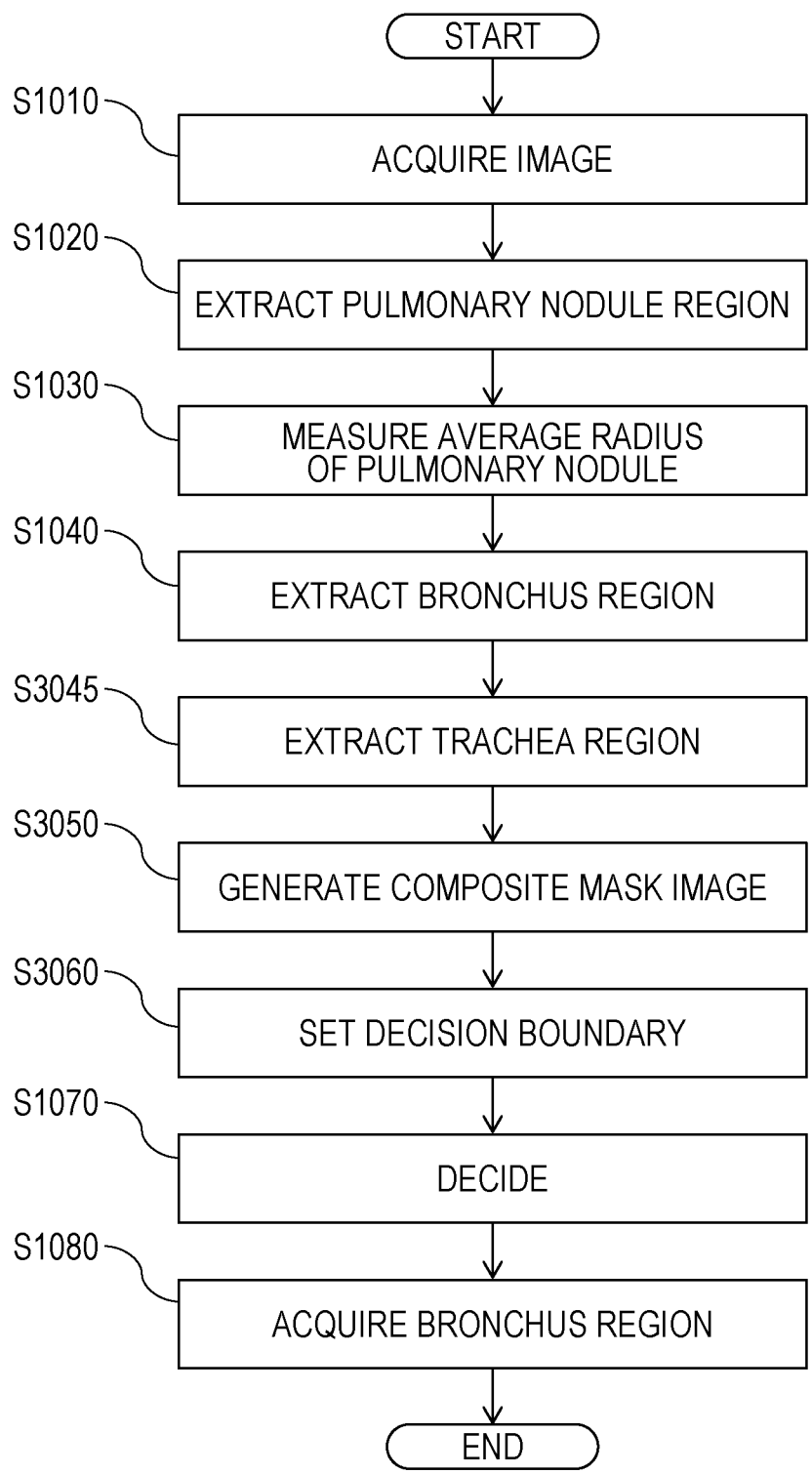
FIG. 15 is a flowchart illustrating an example of processing procedure of the image processing apparatus according to the third embodiment.

Next, processing procedure of the image processing apparatus 300 of the present embodiment will be described with reference to FIG. 15. The image processing apparatus 300 according to the present embodiment performs the processing of steps S1010, S1020, S1030, and S1040 executed by the image processing apparatus 100 according to the first embodiment. Then, the image processing apparatus 300 performs processing of steps S3045, S3050, and S3060 described below.

(S3045)

At step S3045, the third extraction unit 3070 extracts a region (trachea region) of a trachea that exists in the original image. It is to be noted that the trachea region is only required to be almost extracted in the present step in consideration of processing subsequent to step S3050.

The third extraction unit 3070 acquires the original image from the storage unit 120. The third extraction unit 3070 extracts the trachea region by using a known image segmentation method. The trachea region is a tubular organ containing air therein. Therefore, the trachea region has an image feature similar to that of a bronchus region. Thus, the third extraction unit 3070 extracts the trachea region by performing processing equivalent to the processing performed at step S1040 by the image processing apparatus 100 according to the first embodiment. However, in a case where the processing equivalent to that of step S1040 is performed, the bronchus region may be also extracted. In such a case, the bronchus region is excluded by using that the trachea region (1) exists in mediastinum (region surrounded by right and left lungs, thoracic vertebrae, and sternum) and (2) is thicker than the bronchus region.

The third extraction unit 3070 acquires an extraction result in a format of a masked image (trachea masked image $M^{trachea}$). The acquired trachea masked image is saved in the storage unit 120.

Figure 17:
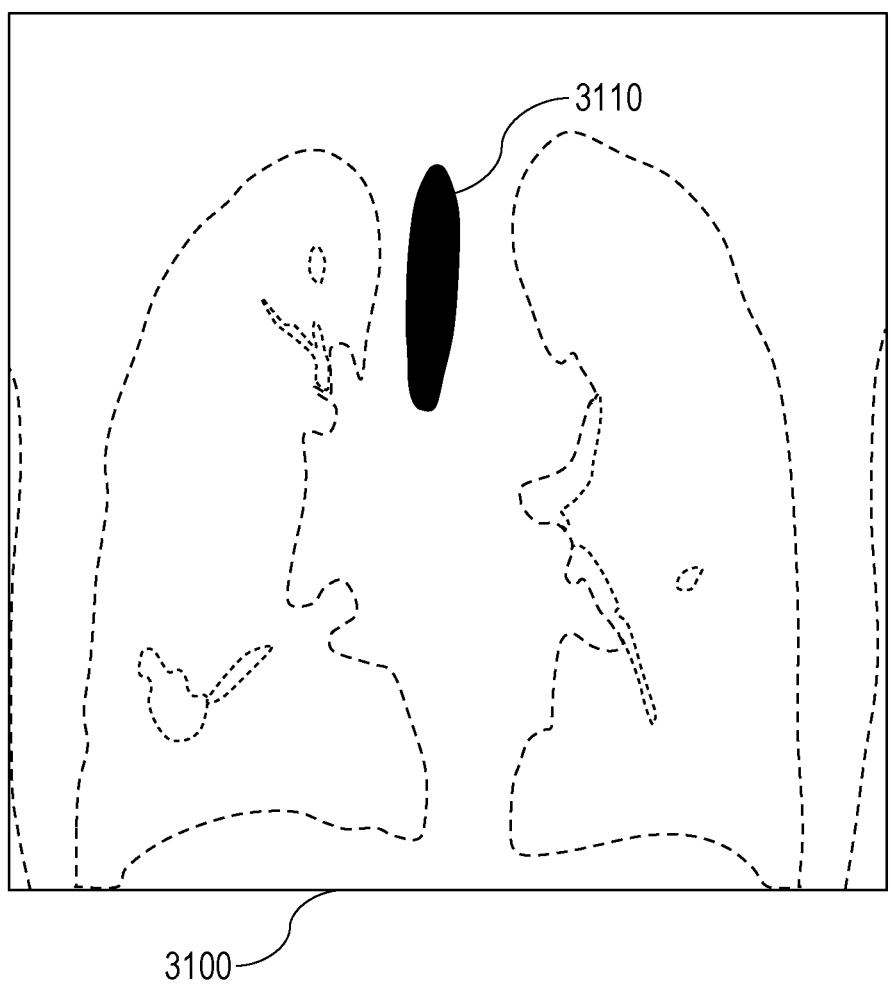
FIG. 17 is a schematic view illustrating an example of a bronchus region extracted from an original image.

FIG. 17 illustrates an example of the trachea region extracted by the third extraction unit 3070. An image 3100 of FIG. 17 is the trachea masked image $M^{trachea}$. A region 3110 is a trachea region $V^{trachea}$.

Though description has been given so far for an example in which the third extraction unit 3070 acquires the trachea region $V^{trachea}$ in the present step, the third extraction unit 3070 may extract a region of a main bronchus in the present step. As the main bronchus, there are two main bronchi of a right main bronchus and a left main bronchus. Thus, the third extraction unit 3070 separately extracts a right main bronchus region $V^{rmainbronchus}$ and a left main bronchus region $V^{lmainbronchus}$. Each of the main bronchus regions is a region directly connected to the trachea region. Thus, by executing a region extension method with the trachea region as an extension start point, the main bronchus region is able to be acquired. The right main bronchus region $V^{rmainbronchus}$ and the left main bronchus region $V^{lmainbronchus}$ respectively exist on a left side and a right side of the trachea region $V^{trachea}$. Therefore, by dividing the region obtained by the region extension method into left and right with the trachea region $V^{trachea}$ as a reference, the right main bronchus region $V^{rmainbronchus}$ and the left main bronchus region $V^{lmainbronchus}$ are able to be acquired.

(S3050)

At step S3050, the setting unit 3040 generates a composite masked image $M^{composite3}$. The composite masked image $M^{composite3}$ is a four-value masked image and respective pixels take four values of 0, 1, 2, and 3. Here, the pixel value 1 indicates that the pixel is a pixel belonging to the pulmonary nodule region. The pixel value 2 indicates that the pixel is a pixel belonging to the candidate region. The pixel value 3 indicates that the pixel is a pixel belonging to the trachea region. The pixel value 0 indicates that the pixel is a pixel not belonging to any of the pulmonary nodule region, the candidate region, and the trachea region. Hereinafter, pixels whose pixel values are 1, 2, 3, and 0 are respectively called a pulmonary nodule pixel, a candidate pixel, a trachea pixel, and a background pixel. Note that, allocation of the pixel values to the respective regions is not limited to the example described above.

The processing of the present step is the same as the processing performed at step S1050 by the setting unit 1040 of the image processing apparatus 100 according to the first embodiment. However, a difference lies in that the composite masked image $M^{composite3}$ is generated from three masked images of a pulmonary nodule masked image $M^{nodule}$, a candidate masked image $M^{candidate}$, and a trachea masked image $M^{trachea}$.

Figure 18:
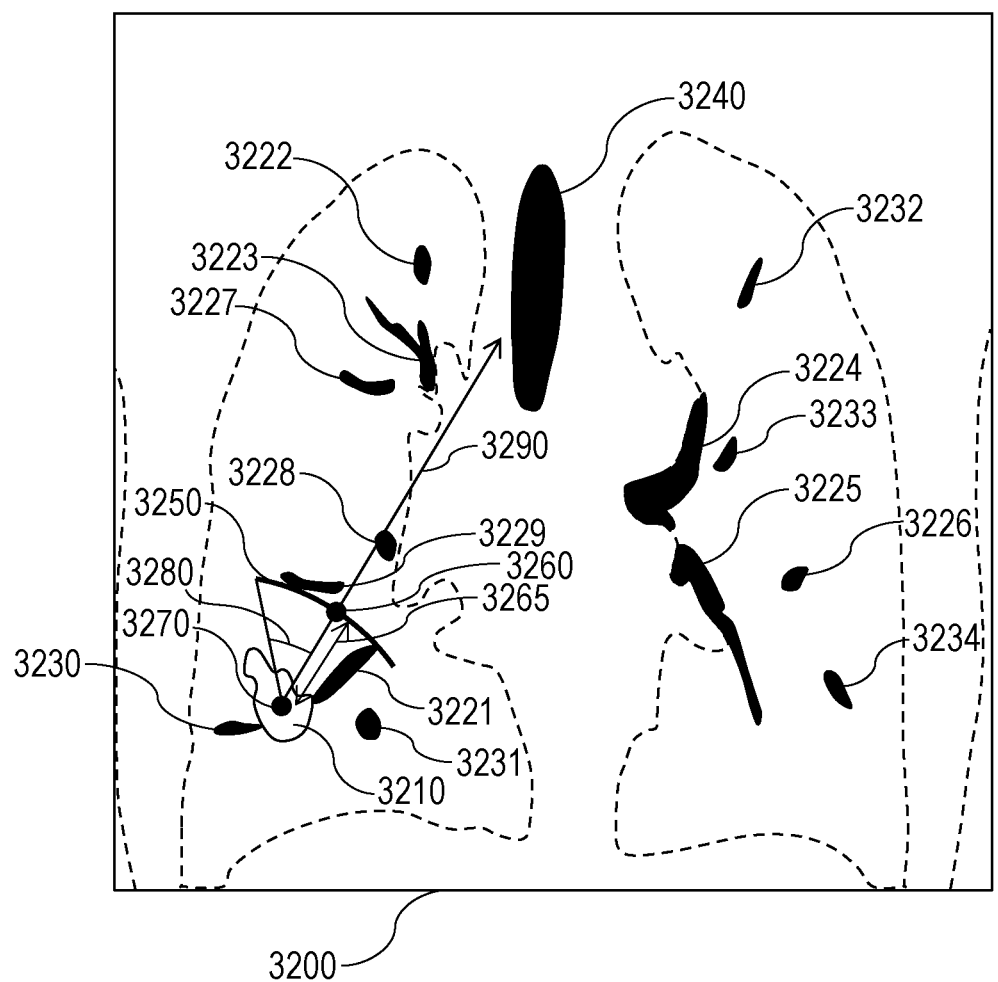
FIG. 18 is a schematic view for explaining an example of a decision boundary set by the image processing apparatus according to the third embodiment.

FIG. 18 illustrates an example of the composite masked image $M^{composite3}$ generated at the present step. An image 3200 of FIG. 18 is the composite masked image $M^{composite3}$. In the composite masked image 3200, a region 3210 is the pulmonary nodule region $V^{nodule}$ extracted at step S1020. Regions 3221 to 3234 are the candidate regions $V^{candidate}_{[i]}$ extracted at step S1040. Among the candidate regions, the candidate regions 3221 to 3226 are regions correctly extracted from the bronchus regions 3081 to 3086 drawn in the original image 3000 of FIG. 16. On the other hand, the candidate regions 3227 to 3234 are not bronchus regions but are erroneously extracted as bronchus regions. Finally, a region 3240 is the trachea region $V^{trachea}$ extracted at step S3045. Note that, an arc 3250, a black point 3260, an arrow 3265, a black point 3270, a solid angle 3280, and an arrow 3290 are information applied to $M^{composite3}$ at step S3060 described below.

(S3060)

At step S3060, the setting unit 3040 sets a decision boundary. The decision boundary will be specifically described with reference to FIG. 18.

At step S3060, the setting unit 3040 sets the decision boundary to the composite masked image $M^{composite3}$. The arc 3250 of FIG. 18 is the decision boundary set by the setting unit 3040. Though the decision boundary 3250 is drawn with the arc in FIG. 18 due to limitation of a drawing, when all tomographic images of the composite masked image $M^{composite3}$ are cross-sectionally observed, it is found that the decision boundary is represented by a part of a surface of an ellipsoid. As found from FIG. 18, the decision boundary set by the setting unit 3040 is represented by a part of a surface of a sphere or ellipsoid in a three-dimensional space. Note that, a shape of the decision boundary may be represented by a part of a plane. It is also possible to use any curved surface for the decision boundary.

For setting the decision boundary 3250, the setting unit 3040 determines a position, an orientation, and a range of the decision boundary. A determination method will be described below.

(Position of Decision Boundary)

The setting unit 3040 sets the decision boundary in a region between the pulmonary nodule region and the trachea region. More specifically, the setting unit 3040 sets the decision boundary 3250 so that a center 3265 of the decision boundary is positioned on a straight line 3290 that connects a centroid position 3270 of the pulmonary nodule region and a centroid position $G^{trachea}$ (not illustrated) of the trachea region 3240. The coordinate value $G^{nodule}$ of the centroid position of the pulmonary nodule region has been already calculated at step S1030 and stored in the storage unit 120. Thus, the setting unit 3040 acquires the coordinate value $G^{nodule}$ of the centroid position of the pulmonary nodule region from the storage unit 120. A coordinate value $G^{trachea}$ of the centroid position of the trachea region is calculated by using the mathematical formula 1. When the centroid position $G^{nodule}$ of the pulmonary nodule region and the centroid position $G^{trachea}$ of the trachea region are calculated, a direction vector $D^{decision3}$ representing the straight line 3290 is calculated by a formula 6.

$$D^{decision3} = G^{trachea} - G^{nodule} = \frac{1}{|G^{trachea} - G^{nodule}|}$$
$$(G_x^{trachea} - G_x^{nodule}, G_y^{trachea} - G_y^{nodule}, G_z^{trachea} - G_z^{nodule})$$

After determining the straight line 3290 for setting the decision boundary, the setting unit 3040 determines a distance $L^{decision3}$ from the pulmonary nodule region 3210 to the decision boundary 3250. The distance $L^{decision3}$ is a distance indicated by the arrow 3265 in FIG. 18. The distance $L^{decision3}$ is determined by the same method as a method of determining a range of the decision boundary, so that description thereof will be given later.

(Orientation of Decision Boundary)

The setting unit 3040 sets an orientation of the decision boundary as a direction from the pulmonary nodule region to the trachea region. The arrow 3290 of FIG. 18 indicates the direction from the pulmonary nodule region to the trachea region. The direction matches the direction vector $D^{decision3}$ calculated by the mathematical formula 6. Thus, the setting unit 3040 uses $D^{decision3}$ as the direction of the decision boundary.

(Distance from Decision Boundary to Pulmonary Nodule Region and Range of Decision Boundary)

The setting unit 3040 determines the distance $L^{decision3}$ and the range of the decision boundary on the basis of a size of the pulmonary nodule region $V^{nodule}$. Here, the range of the decision boundary is represented by a solid angle $\theta^{decision3}$ (solid angle 3280 in FIG. 18) with the centroid position of the pulmonary nodule region as a base point. Note that, the range of the decision boundary is represented by using the solid angle here, but may be represented by any format as long as the range of the decision boundary is able to be represented.

The setting unit 3040 determines the solid angle $\theta^{decision3}$ and the distance $L^{decision3}$ on the basis of the average radius $R^{nodule}$ of the pulmonary nodule region $V^{nodule}$. A specific determination method conforms to the method performed at step S1060 by the image processing apparatus 100 according to the first embodiment. Thus, description will be given briefly here. Note that, the solid angle $\theta^{decision3}$ and the distance $L^{decision3}$ may be determined on the basis of information (such as an average diameter, a maximum radius, a median value of radiuses) other than the average radius of the pulmonary nodule region. The setting unit 3040 acquires a list $L_3$ from the data server 130. In the list $L_3$, (average radius $R^{nodule}_{[k]}$ of pulmonary nodule region, distance $L^{decision}_{[k]}$ from pulmonary nodule region to decision boundary, range $\theta^{decision}_{[k]}$ of decision boundary) (in which, $1<=k<=N^{L3}$) are stored. After acquiring the list $L_3$ from the data server 130, the setting unit 3040 compares each $R^{nodule}_{[k]}$ stored in $L_3$ to $R^{nodule}$ and searches for a value $R^{nodule}_{[k']}$, ($1<=k'<=N^{L3}$) closest to $R^{nodule}$. A distance $L^{decision}_{[k']}$ from the pulmonary nodule region to the decision boundary and a range $\theta^{decision}_{[k']}$ of the decision boundary that are paired with $R^{nodule}_{[k']}$ are respectively used as the distance from the pulmonary nodule region to the decision boundary and the range of the decision boundary. Note that, a method of establishing the list $L_3$ is as described in the explanation for the first embodiment, but is different from that of the list $L_1$ of the first embodiment only in data that is included.

This is the end of the description for the method of determining the decision boundary.

The setting unit 3040 thus determines the position, the orientation, and the range of the decision boundary. Finally, the setting unit 3040 sets the decision boundary in the composite masked image $M^{composite3}$. A method thereof is also as described in the explanation for step S1060. Though the sphere is drawn in the processing of step S1060, the shape of the decision boundary defined by the setting unit 3040 is drawn in the composite masked image in the present step.

After finishing all the processing described above, the setting unit 3040 saves the composite masked image $M^{composite3}$ in the storage unit 120.

The method of determining the position, the orientation, and the range of the decision boundary by using the trachea region $V^{trachea}$ has been described above. However, in a case where the third extraction unit 3070 extracts a main bronchus region at step S3045, the main bronchus region may be used instead of the trachea region $V^{trachea}$ in the present step. For example, in a case where a pulmonary nodule region that is currently of interest exists in a right lung field region, a centroid position $G^{rmainbronchus}$ of a right main bronchus region $V^{rmainbronchus}$ is calculated first by using the mathematical formula 1. Then, a direction vector $D^{decision3}$ directed from a centroid position $G^{nodule}$ of the pulmonary nodule region to the centroid position of the right main bronchus region $V^{rmainbronchus}$ may be calculated by using the following mathematical formula 7.

$$D^{decision3} =$$
$$G^{rmainbronchus} - G^{nodule} = \frac{1}{|G^{rmainbronchus} - G^{nodule}|}(G_x^{rmainbronchus} - G_x^{nodule},$$
$$G_y^{rmainbronchus} - G_y^{nodule}, G_z^{rmainbronchus} - G_z^{nodule})$$

In a case where the pulmonary nodule region that is currently of interest exists in the right lung field region, the left main bronchus region $V^{lmainbronchus}$ may be used instead of the right main bronchus region $V^{rmainbronchus}$.

This is the end of the description for the processing performed by the setting unit 3040 at step S3060.

After finishing the processing of step S3060, the image processing apparatus 300 according to the third embodiment performs the processing of steps S1070 and S1080. The processing performed at the steps is as described in the explanation for the first embodiment.

Figure 19:
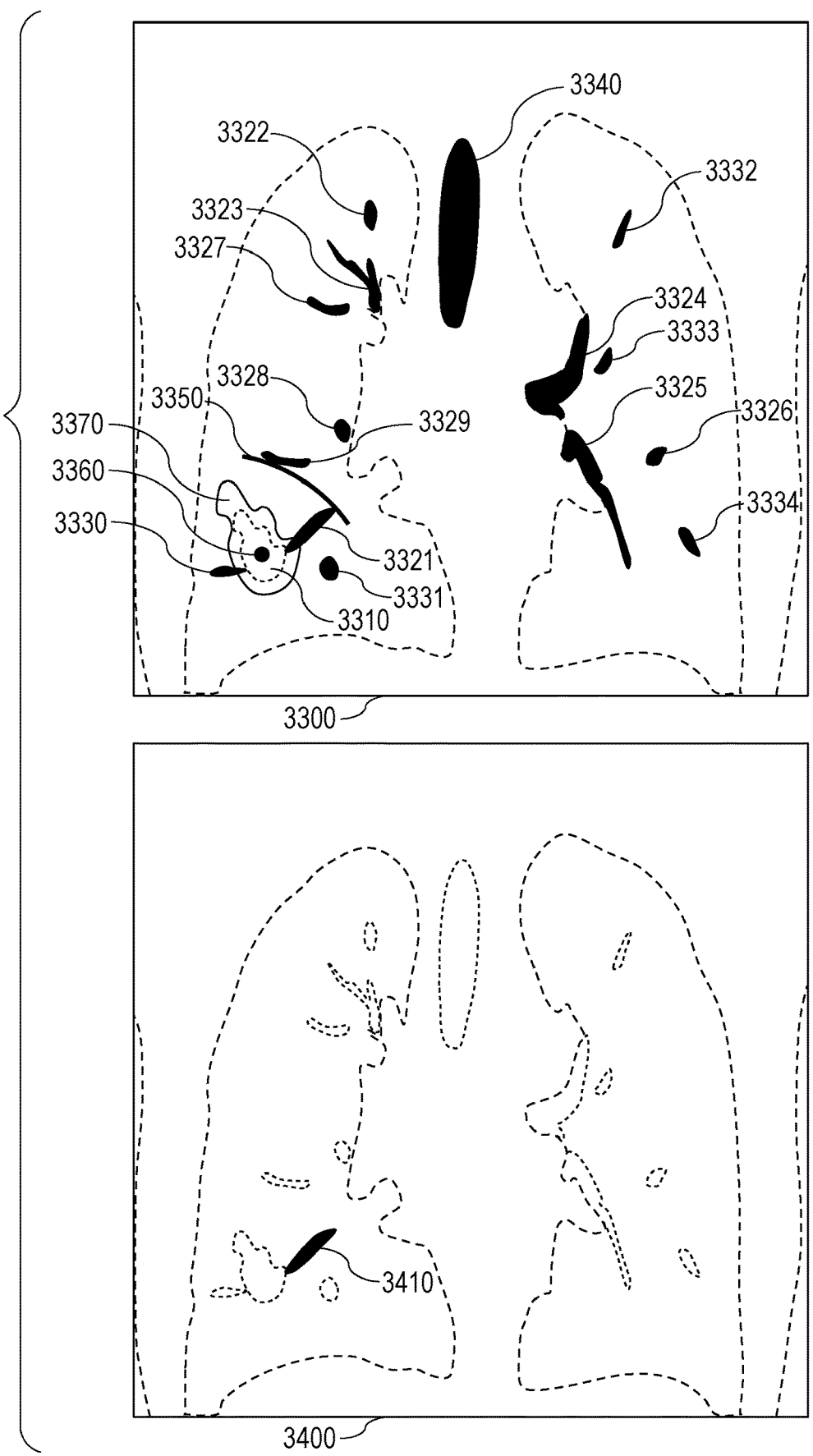
FIG. 19 is a schematic view illustrating an example of decision processing performed by the image processing apparatus according to the third embodiment and a processing result thereof.

Here, processing results of steps S1070 and S1080 of the image processing apparatus 300 according to the present embodiment will be checked with reference to FIG. 19.

An image 3300 of FIG. 19 is the composite masked image $M^{composite3}$. In the composite masked image 3300, a region 3370 surrounded by a solid line is an extension region $V^{nodule'}$. The extension region 3370 is a region obtained by dilating a pulmonary nodule region 3310, which is surrounded by a broken line, with a black point 3360 as the center. Note that, the black point 3360 is a centroid position of the pulmonary nodule region 3310. Note that, processing for dilating the pulmonary nodule region 3310 is not essential processing.

Since a candidate region 3321 contacts (overlaps) with both the extension region 3370 and a decision boundary 3350, the decision result is "true". Since a candidate region 3329 contacts (overlaps) with the decision boundary 3350 but does not contact (overlap) with the extension region 3370, the decision result is "false". To the contrary, since a candidate region 3330 contacts (overlaps) with the extension region 3370 but does not contact (overlap) with the decision boundary 3350, the decision result is "false". Since candidate regions 3322 to 3328 and candidate regions 3331 to 3334 contact (overlap) with neither the extension region 3370 nor the decision boundary 3350, the decision results are "false".

An image 3400 of FIG. 19 is the bronchus masked image $M^{bronchus}$ acquired at step S1080. The image 3400 is obtained as a result of applying the processing of step S1080 to the candidate regions 3321 to 3334 of the composite masked image 3300. According to the processing of step S1070, the decision result for only the candidate region 3321 is "true" and the decision results for the other candidate regions are "false". On the basis of the decision results, the candidate region 3321 is acquired as a desired region 3410 at step 1080. The candidate regions (the candidate regions 3322 to 3334) other than the candidate region 3321 are not acquired as the desired region 3410.

In accordance with the foregoing procedure, the image processing apparatus 300 according to the third embodiment performs processing for extracting the bronchus running around the target pulmonary nodule.

Now, processing for extracting an artery and vein running around the target pulmonary nodule by the image processing apparatus 300 according to the third embodiment will be described. In the processing performed by the image processing apparatus 300 according to the third embodiment, the processing of steps S1010, S1020, and S1030 is performed in the same manner also in the extraction of an artery and vein region. At step S1040, the second extraction unit 1020 extracts not the bronchus region but candidate regions of the artery and vein in a lung field. The processing for extracting the artery and vein region is as described in the explanation for the first embodiment. At step S3045, the third extraction unit 3070 extracts not the trachea region but a pulmonary artery and vein region in mediastinum. A known image segmentation method is used for the extraction of the pulmonary artery and vein region in the mediastinum. At steps S3050, S3060, S1070, and S1080, similar processing to the processing in the extraction of the bronchus region may be performed.

In accordance with the foregoing procedure, the image processing apparatus 300 according to the third embodiment performs processing for extracting the artery and vein running around the target pulmonary nodule.

The image processing apparatus 300 according to the third embodiment is able to extract a region of a structure (bronchus or artery and vein) running around the target pulmonary nodule by the processing described above with higher accuracy than conventional one. That is, a bronchus or an artery and vein that is related to the target pulmonary nodule among bronchi or arteries and veins is able to be extracted with high accuracy. In other words, a bronchus or an artery and vein that is likely to be particularly focused on by a doctor among bronchi or arteries and veins is able to be extracted with high accuracy. Additionally, according to the third embodiment, since the decision boundary is provided between the nodule region and the trachea region and the decision boundary is not provided in a direction opposite to a direction directed from the nodule region to the trachea region, a bronchus or an artery and vein that is related to the target pulmonary nodule among bronchi or arteries and veins is able to be extracted with high accuracy.

Note that, the third embodiment and the second embodiment may be combined. For example, though the decision boundary is provided in four sides of the composite masked image in FIG. 12 in the second embodiment, the decision boundary may be provided only in a side existing between the nodule region and the trachea region among the four sides of the composite masked image. This makes it possible to achieve effects of both the second embodiment and the third embodiment.

Fourth Embodiment

An image processing apparatus according to a fourth embodiment sets a decision boundary in a region where a bronchus is expected to run on the basis of a position of a pulmonary nodule in a lung field. Then, the image processing apparatus acquires a region of a desired bronchus by using the set decision boundary. The image processing apparatus according to the fourth embodiment will be described below.

Figure 20:
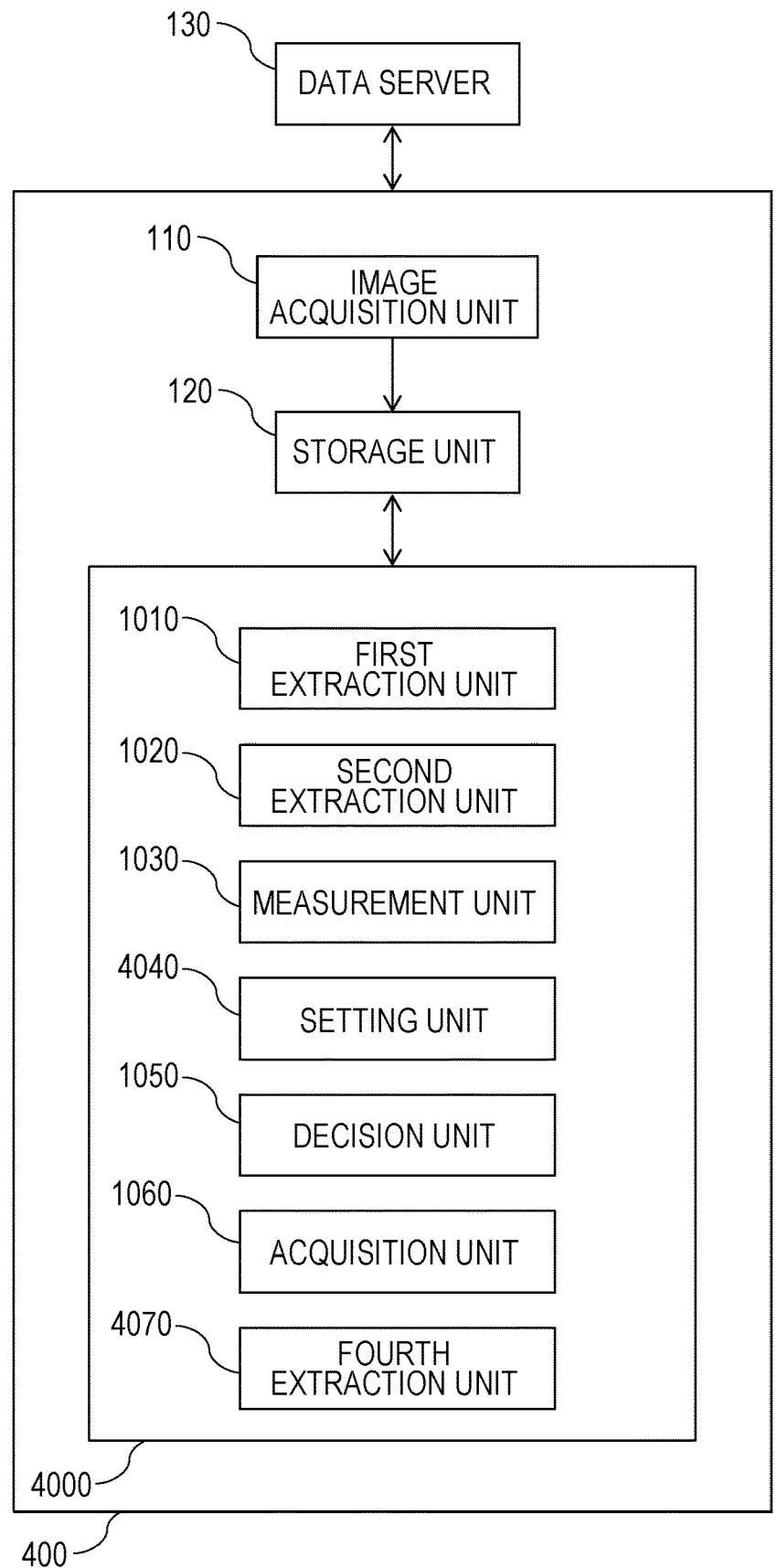
FIG. 20 illustrates an example of a functional configuration of the image processing apparatus according to the fourth embodiment.

A functional configuration of the image processing apparatus according to the present embodiment will be described with reference to FIG. 20. An image processing unit 4000 of an image processing apparatus 400 according to the fourth embodiment includes a first extraction unit 1010, a second extraction unit 1020, a measurement unit 1030, a setting unit 4040, a decision unit 1050, an acquisition unit 1060, and a fourth extraction unit 4070. Similarly to the first embodiment, functions of the aforementioned units are realized by one or more processors included in the image processing apparatus 400. Among the processing units, processing units other than the setting unit 4040 and the fourth extraction unit 4070 perform the same processing as the processing units in the image processing apparatus 100 according to the first embodiment. Thus, description for the processing units will be omitted.

The setting unit 4040 generates a composite masked image from a pulmonary nodule masked image, a candidate masked image, and a lung field masked image. Next, the setting unit 4040 sets a decision boundary in the composite masked image on the basis of a position of a pulmonary nodule region in a lung field region. Finally, the setting unit 4040 saves the composite masked image in the storage unit 120.

The fourth extraction unit 4070 acquires an original image from the storage unit 120. Then, the fourth extraction unit 4070 applies a known image segmentation method to the original image and extracts a lung field region drawn in the original image. The fourth extraction unit 4070 acquires an extraction result in a format of a masked image (lung field masked image). The acquired lung field masked image is saved in the storage unit 120.

Figure 21:
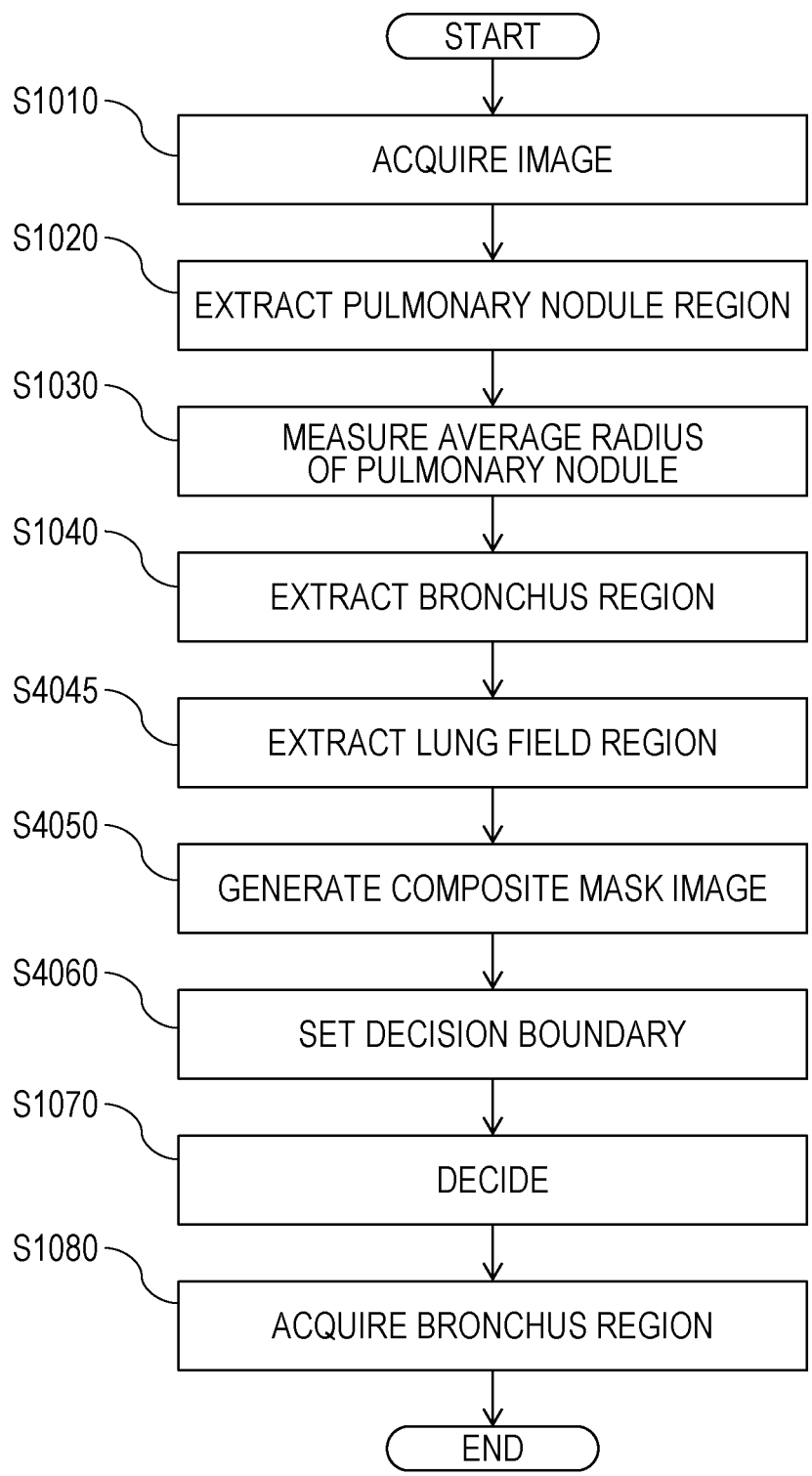
FIG. 21 is a flowchart illustrating an example of processing procedure of the image processing apparatus according to the fourth embodiment.

Next, processing procedure of the image processing apparatus 400 of the present embodiment will be described with reference to FIG. 21. The image processing apparatus 400 according to the present embodiment performs the processing of steps S1010, S1020, S1030, and S1040 executed by the image processing apparatus 100 according to the first embodiment. Then, the image processing apparatus 400 performs processing of steps S4045, S4050, and S4060 described below.

(S4045)

At step S4045, the fourth extraction unit 4070 acquires the original image from the storage unit 120. The fourth extraction unit 4070 extracts a region (lung field region) of a lung field that exists in the original image. The lung field region has an almost constant CT value in a CT image. Thus, by using a known image segmentation method (such as threshold processing, a region extension method, a level-set method, or a graph-cut method), the lung field region is able to be extracted.

The fourth extraction unit 4070 acquires information of the extracted lung field region in a format of a masked image (lung field masked image $M^{lung}$). The acquired lung field masked image is saved in the storage unit 120.

Figure 22:
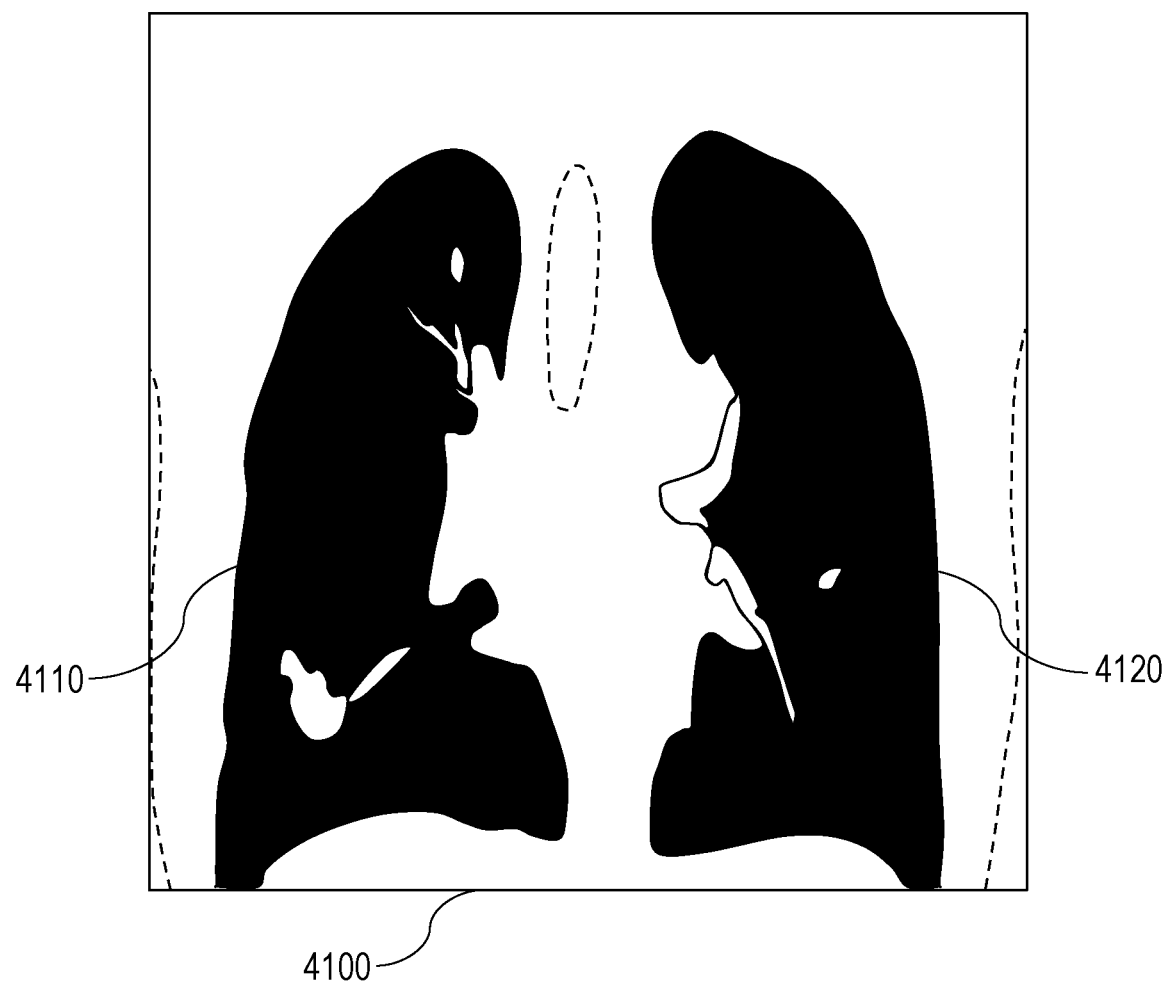
FIG. 22 is a schematic view illustrating an example of a lung field region extracted from an original image.

FIG. 22 illustrates an example of the lung field region extracted by the fourth extraction unit 4070. An image 4100 of FIG. 22 is the lung field masked image $M^{lung}$. A region 4110 and a region 4120 are regions of a right lung field and a left lung field extracted by the fourth extraction unit 4070. The regions are collectively referred to as $V^{lung}$.

(S4050)

At step S4050, the setting unit 4040 generates a composite masked image $M^{composite4}$. The composite masked image $M^{composite4}$ is a four-value masked image and respective pixels take four values of 0, 1, 2, and 3. Here, the pixel value 1 indicates that the pixel is a pixel belonging to the pulmonary nodule region. The pixel value 2 indicates that the pixel is a pixel belonging to the candidate region. The pixel value 3 indicates that the pixel is a pixel belonging to the lung field region. The pixel value 0 indicates that the pixel is a pixel not belonging to any of the pulmonary nodule region, the candidate region, and the lung field region. Pixels whose pixel values are 1, 2, 3, and 0 are respectively called a pulmonary nodule pixel, a candidate pixel, a lung field pixel, and a background pixel. Note that, allocation of the pixel values to the respective regions is not limited to the example described above.

The processing of the present step is the same as the processing performed at step S1050 by the setting unit 1040 of the image processing apparatus 100 according to the first embodiment. However, a difference lies in that the composite masked image $M^{composite4}$ is generated from three masked images of a pulmonary nodule masked image $M^{nodule}$, a candidate masked image $M^{candidate}$, and a lung field masked image $M^{lung}$.

Figure 23:
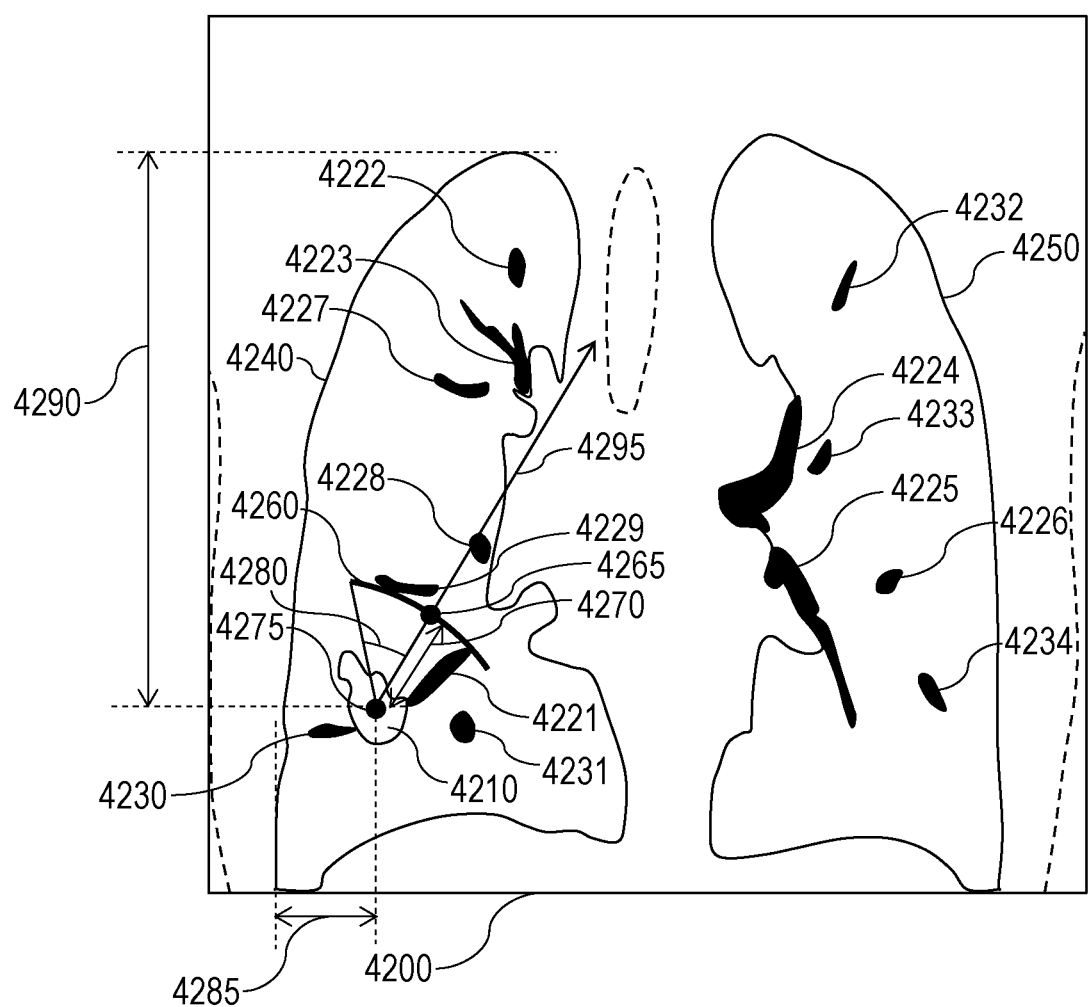
FIG. 23 is a schematic view for explaining an example of a decision boundary set with use of a list $L_{41}$ by the image processing apparatus according to the fourth embodiment.

FIG. 23 illustrates an example of the composite masked image $M^{composite4}$ generated at the present step. An image 4200 of FIG. 23 is the composite masked image $M^{composite4}$. In the composite masked image 4200, a region 4210 is the pulmonary nodule region $V^{nodule}$ extracted at step S1020. Regions 4221 to 4234 are the candidate regions $V^{candidate}_{[i]}$ extracted at step S1040. Among the candidate regions, the candidate regions 4221 to 4226 are regions correctly extracted from the bronchus regions 3081 to 3086 drawn in the original image 3000 of FIG. 16. On the other hand, the candidate regions 4227 to 4234 are not bronchus regions but are erroneously extracted as bronchus regions. Finally, regions surrounded by a solid line 4240 and a solid line 4250 are the lung field regions $V^{lung}$ extracted at step S4045. Note that, a curved surface 4260, a black point 4265, an arrow 4270, a black point 4275, a solid angle 4280, an arrow 4285, an arrow 4290, and an arrow 4295 are information applied to $M^{composite4}$ at step S4060 described below.

(S4060)

At step S4060, the setting unit 4040 sets a decision boundary to the composite masked image $M^{composite4}$. A method of setting the decision boundary will be specifically described with reference to FIGS. 23 and 25.

(Position of Decision Boundary)

The setting unit 4040 sets the decision boundary on the basis of a position of the pulmonary nodule region in the lung field region. First, the setting unit 4040 acquires a coordinate value $G^{nodule}$ of a centroid position of the pulmonary nodule region from the storage unit 120. Then, the setting unit 4040 acquires positions ($S_x$, $S_y$, $S_z$) of the pulmonary nodule region $V^{nodule}$ in the lung field region $V^{lung}$. Here, the positions ($S_x$, $S_y$, $S_z$) are set as distances from an outer side, an upper end, an abdomen side end of the lung field region. In FIG. 23, since distances indicated by the arrow 4285 and the arrow 4290 are respectively $S_x$ and $S_y$. For simplicity of the drawing, the position $S_z$ is not illustrated. In a case where the pulmonary nodule region $V^{nodule}$ exists in the right lung, the position $S_x$ is set as a distance from the outer side of the right lung. To the contrary, in a case where the pulmonary nodule region $V^{nodule}$ exists in the left lung, the position $S_x$ is set as a distance from the outer side of the left lung. In FIG. 23, the pulmonary nodule region 4210 exists in the right lung, the value of the position $S_x$ is the distance 4285 from the outer side of the right lung. Regardless of whether the pulmonary nodule region exists in the right lung or the left lung, the position $S_x$ may be a distance from the inner side of the lung field region. The position $S_y$ may be a distance from a lower end of the lung field region. The position $S_z$ may be a distance from a back side end of the lung field region. Further, values obtained by dividing the respective positions by a length from an upper end to a lower end, a length from a right end to a left end, and a length from an abdomen side end to a back side end in the lung field region may be used. That is, the positions $(S_x, S_y, S_z)=(S_x/W^{lung}, S_y/H^{lung}, S_z/D^{lung})$ may be used. Here, $W^{lung}$, $H^{lung}$, and $D^{lung}$ are respectively the length from the upper end to the lower end, the length from the right end to the left end, and the length from the abdomen side end to the back side end in the lung field region.

Next, the setting unit 4040 acquires a list $L_4$ from the data server 130 via the storage unit 120. A plurality of sets of two numerical values of (positions $(S_{x[k]}, S_{y[k]}, S_{z[k]})$, direction vector $D^{decision4}_{[i]}$) ($1<=k<=N^L_4$) are stored in the list $L_4$.

After acquiring the list $L_4$ from the data server 130, the setting unit 4040 compares each $(S_{x[k]}, S_{y[k]}, S_{z[k]})$ stored in $L_4$ to $(S_x, S_y, S_z)$ and searches for a value $(S_{x[k']}, S_{y[k']}, S_{z[k']})$ ($1<=k'<=N^L_4$) closest to $(S_x, S_y, S_z)$. Then, a direction vector $D^{decision4}_{[k']}$ of the decision boundary that is paired with $(S_{x[k']}, S_{y[k']}, S_{z[k']})$ is used as a direction vector of the decision boundary set to the composite masked image $M^{composite4}$.

Here, the list $L_4$ will be described. The list $L_4$ is established from a learning image prepared in advance. Procedure of establishing the list $L_4$ is similar to the procedure of establishing the list $L_1$ or $L_3$.

The setting unit 4040 is able to use, as the list $L_4$, any one of a list $L_{41}$ and a list $L_{42}$ in which two types of direction vectors having different features are stored. The direction vectors stored in the list $L_{41}$ and the list $L_{42}$ have features different from each other. Thus, a person who establishes the image processing apparatus 400 according to the fourth embodiment selects any one of the list $L_{41}$ and the list $L_{42}$ as the list $L_4$ at a stage of establishing the image processing apparatus 400. At a stage of executing the image processing apparatus 400, an operator of the image processing apparatus 400 may be caused to select any one of the lists via an operation unit which is not illustrated in FIG. 20. In such a case, the setting unit 4040 uses, as the list $L_4$, the list selected by the operator. A method of determining each of the lists $L_{41}$ and $L_{42}$ will be described below.

First, the direction vector $D^{decision4}_{[k]}$ of the list $L_{41}$ will be described. In the direction vector $D^{decision4}_{[k]}$ of the list $L_{41}$, a relative position of a trachea region to the centroid position of the pulmonary nodule region or a relative position of a bronchus region in a pulmonary hilum is stored. Specific description will be given with reference to FIG. 23. The image 4200 of FIG. 23 is the composite masked image $M^{composite4}$ obtained by applying the processing of steps S1010 to S4050 to the original image 3000 of FIG. 16. In a case where the list $L_{41}$ is used as the list $L_4$, the setting unit 4040 sets the direction vector 4295 as a direction of the decision boundary. Here, the direction vector 4295 is a direction vector directed from the centroid position 4275 of the pulmonary nodule region 4210 to the trachea region indicated by a dotted line. That is, when the centroid position of the pulmonary nodule region in the original image is obtained, the position of the trachea region or the bronchus region drawn in the original image is able to be acquired.

Learning images are used to determine the direction vector $D^{decision4}_{[k]}$ of the list $L_{41}$. First, a coordinate value of the centroid position of the pulmonary nodule is acquired in each of the learning images. Next, a coordinate value of a centroid position of the bronchus in the trachea or the pulmonary hilum is acquired. The positions are manually acquired from each of the learning images. Finally, the coordinate value of the centroid of the bronchus in the trachea or the pulmonary hilum is set as a relative coordinate value from the centroid position of the pulmonary nodule.

This is the end of the description of the direction vector $D^{decision4}_{[k]}$ of the list $L_{41}$.

Figure 25:
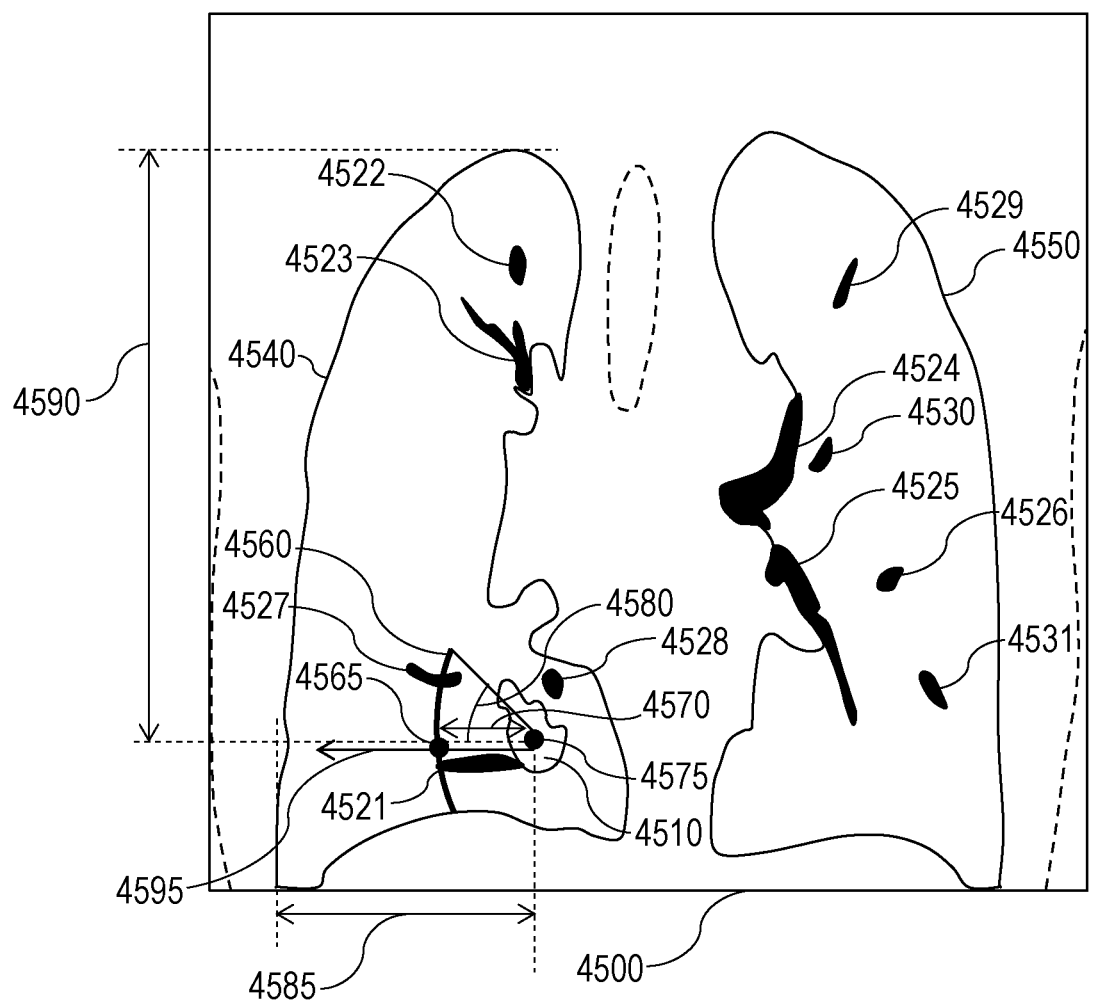
FIG. 25 is a schematic view for explaining an example of a decision boundary set with use of a list $L_{42}$ by the image processing apparatus according to the fourth embodiment.

Next, the direction vector $D^{decision4}_{[k]}$ of the list $L_{42}$ will be described. In the direction vector $D^{decision4}_{[k]}$ of the list $L_{42}$, a position of a region of a bronchus of interest in an image is stored as a relative position to the centroid position of the pulmonary nodule region. Specific description will be given with reference to FIG. 25. An image 4500 of FIG. 25 is the composite masked image $M^{composite4}$ obtained by applying the processing of steps S1010 to S4050 to an original image (not illustrated).

In the image 4500, a pulmonary nodule region 4510 exists in a place near a lung base and close to mediastinum in the lung field region. In such a place, the bronchus does not run from a direction of the bronchus in the trachea or the pulmonary hilum. Instead, the bronchus runs along the lung base. A bronchus region 4521 is an example of the bronchus running along the lung base. In FIG. 25, the bronchus region 4521 is a bronchus region (desired bronchus region) desired to be extracted. Note that, though an example of the lung base is taken in FIG. 25, the place of the target bronchus varies depending on a place in the lung field region.

In a case where the list $L_{42}$ is used as the list $L_4$, the setting unit 4040 sets the direction along the direction in which the target bronchus runs as the direction of the decision boundary in accordance with the place of the pulmonary nodule region in the lung field. The setting unit 4040 sets a direction vector 4595 as the direction of the decision boundary in the pulmonary nodule region 4510 of FIG. 25. As found from FIG. 25, the direction vector $D^{decision4}_{[k]}$ of the list $L_{42}$ does not match the relative position of the trachea or the relative position of the bronchus in the pulmonary hilum in some cases. By using the list $L_{42}$ as the list $L_4$, a bronchus region that does not linearly run from a position of a main bronchus in the trachea or the pulmonary hilum is able to be extracted.

Learning images are used to determine the direction vector $D^{decision4}_{[k]}$ of the list $L_{42}$. First, a coordinate value of the centroid position of the pulmonary nodule is acquired in each of the learning images. Next, a coordinate value of a centroid position of the bronchus region desired to be extracted is acquired. The positions are manually acquired from each of the learning images. Finally, the coordinate value of the centroid of the bronchus region desired to be extracted is set as a relative coordinate value from the centroid position of the pulmonary nodule.

This is the end of the description of the direction vector $D^{decision4}_{[k]}$ of the list $L_{42}$.

This is the end of the description of details of the list $L_4$, the list $L_{41}$, and the list $L_{42}$, and an establishing method thereof.

(Orientation of Decision Boundary)

The setting unit 4040 sets $D^{decision3}$ as the orientation of the decision boundary. This is performed similarly to the setting unit 4040 of the image processing apparatus 300 according to the third embodiment.

(Distance from Pulmonary Nodule Region to Decision Boundary and Range of Decision Boundary)

The setting unit 4040 determines a distance $L^{decision4}$ from the pulmonary nodule region 4210 to the decision boundary 4260 and a solid angle $\theta^{decision4}$ indicating a range of the decision boundary.

In FIG. 23, the distance $L^{decision4}$ is a distance indicated by an arrow 4265. The solid angle $\theta^{decision4}$ is a solid angle indicated by the angle 4280. In FIG. 25, the distance $L^{decision4}$ is a distance indicated by an arrow 4570. The solid angle $\theta^{decision4}$ is a solid angle indicated by the angle 4580. A method of determining values thereof is the same as the processing performed at step S3060 by the setting unit 3040 of the image processing apparatus 300 according to the third embodiment. Thus, description thereof will be omitted.

This is the end of the description of the processing performed at step S4060 by the setting unit 4040.

After finishing the processing of step S4060, the image processing apparatus 400 according to the fourth embodiment performs the processing of steps S1070 and S1080. The processing performed at the steps is as described in the explanation for the first embodiment.

Figure 24:
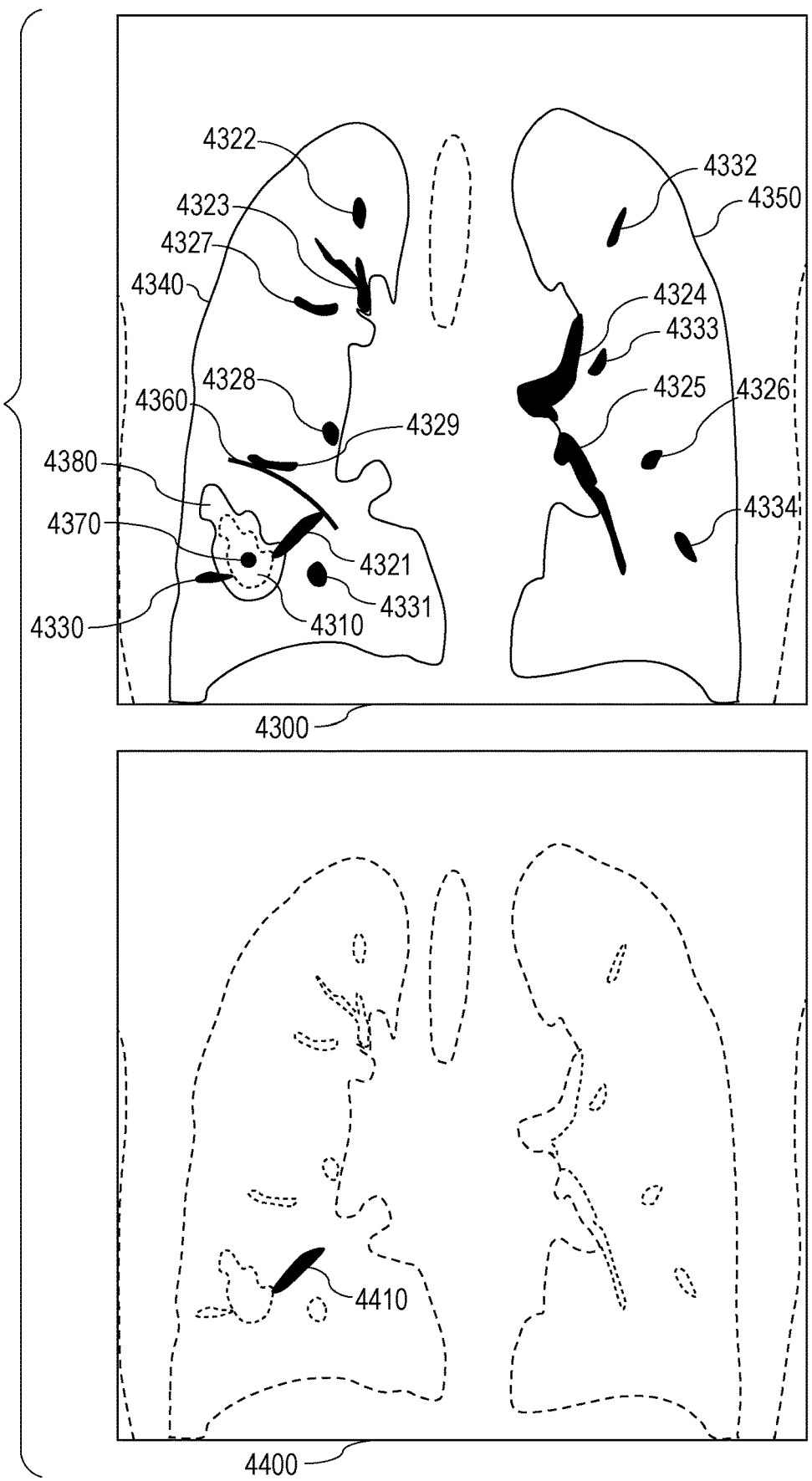
FIG. 24 is a schematic view illustrating an example of decision processing performed on the basis of the decision boundary set with use of the list $L_{41}$ by the image processing apparatus according to the fourth embodiment and an example of a processing result thereof.

Here, processing results of steps S1070 and S1080 of the image processing apparatus 400 according to the present embodiment will be checked with reference to FIG. 24. An image 4300 of FIG. 24 is the composite masked image $M^{composite4}$. Here, the composite masked image 4300 is a composite masked image generated when the list $L_{41}$ is used as the list $L_4$ at step S4060. In the composite masked mage 4300, a region 4380 surrounded by a solid line is an extension region $V^{nodule'}$. The extension region 4380 is a region obtained by dilating a pulmonary nodule region 4310, which is surrounded by a broken line, with a black point 4370 as the center. Note that, the black point 4370 is a centroid position of the pulmonary nodule region 4310. Note that, processing for dilating the pulmonary nodule region 4310 is not essential processing.

Since a candidate region 4321 contacts (overlaps) with both the extension region 4380 and a decision boundary 4360, the decision result is "true". Since a candidate region 4329 contacts (overlaps) with the decision boundary 4360 but does not contact (overlap) with the extension region 4380, the decision result is "false". To the contrary, since a candidate region 4330 contacts (overlaps) with the extension region 4380 but does not contact (overlap) with the decision boundary 4360, the decision result is "false". Since candidate regions 4322 to 4328 and candidate regions 4331 to 4334 contact (overlap) with neither the extension region 4380 nor the decision boundary 4360, the decision results are "false".

An image 4400 of FIG. 24 is the bronchus masked image $M^{bronchus}$ acquired at step S1080. The image 4400 is obtained as a result of applying the processing of step S1080 to the candidate regions 4321 to 4334 of the composite masked image 4300. According to the processing of step S1070, the decision result for only the candidate region 4321 is "true" and the decision results for the other candidate regions are "false". On the basis of the decision results, the candidate region 4321 is acquired as a desired region 4410 at step 1080. The candidate regions (the candidate regions 4322 to 4334) other than the candidate region 4321 are not acquired.

Next, processing results of steps S1070 and S1080 of the image processing apparatus 400 according to the present embodiment will be checked with reference to FIG. 26. An image 4600 of FIG. 26 is the composite masked image $M^{composite4}$. Here, the composite masked image 4600 is a composite masked image generated when the list $L_{42}$ is used as the list $L_4$ at step S4060. In the composite masked mage 4600, a region 4680 surrounded by a solid line is an extension region $V^{nodule'}$. The extension region 4680 is obtained by dilating a pulmonary nodule region 4610, which is surrounded by a broken line, with a black point 4670 as the center. Note that, the black point 4670 is a centroid position of the pulmonary nodule region 4610. Processing for dilating the pulmonary nodule region 4610 is not essential processing.

Since a candidate region 4621 contacts (overlaps) with both the extension region 4680 and a decision boundary 4660, the decision result is "true". Since a candidate region 4627 contacts (overlaps) with the decision boundary 4660 but does not contact (overlap) with the extension region 4680, the decision result is "false". To the contrary, since a candidate region 4628 contacts (overlaps) with the extension region 4680 but does not contact (overlap) with the decision boundary 4660, the decision result is "false". Since candidate regions 4622 to 4626 and candidate regions 4629 to 4631 contact (overlap) with neither the extension region 4680 nor the decision boundary 4660, the decision results are "false".

An image 4700 of FIG. 26 is the bronchus masked image $M^{bronchus}$ acquired at step S1080. The image 4700 is obtained as a result of applying the processing of step S1080 to the candidate regions 4621 to 4631 of the composite masked image 4600. According to the processing of step S1070, the decision result for only the candidate region 4621 is "true" and the decision results for the other candidate regions are "false". On the basis of the decision results, the candidate region 4621 is acquired as a desired region 4710 at step 1080. The candidate regions (the candidate regions 4622 to 4631) other than the candidate region 4621 are not acquired.

In accordance with the foregoing procedure, the image processing apparatus 400 according to the fourth embodiment performs processing for extracting the bronchus running around the target pulmonary nodule.

Now, processing for extracting an artery and vein running around the target pulmonary nodule by the image processing apparatus 400 according to the fourth embodiment will be described. In the processing performed by the image processing apparatus 400 according to the fourth embodiment, the processing of steps S1010, S1020, and S1030 is performed in the same manner also in extraction of an artery and vein region. At step S1040, the second extraction unit 1020 extracts not the bronchus region but candidate regions of the artery and vein. The processing for extracting the artery and vein region is as described in the explanation for the first embodiment. At steps S4045, S4050, S4060, S1070, and S1080, similar processing to the processing in the extraction of the bronchus region may be performed.

In accordance with the foregoing procedure, the image processing apparatus 400 according to the fourth embodiment performs processing for extracting the artery and vein running around the target pulmonary nodule.

The image processing apparatus 400 according to the fourth embodiment is able to extract a region of a structure (bronchus or artery and vein) running around the target pulmonary nodule by the processing described above with higher accuracy than conventional one. That is, a bronchus or an artery and vein that is related to the target pulmonary nodule among bronchi or arteries and veins is able to be extracted with high accuracy. In other words, a bronchus or an artery and vein that is likely to be particularly focused on by a doctor among bronchi or arteries and veins is able to be extracted with high accuracy. Additionally, according to the fourth embodiment, not only a bronchus or an artery and vein that exists between the pulmonary nodule and the trachea and is related to the target pulmonary nodule but also a bronchus or an artery and vein that is other than the bronchus or the artery and vein existing between the pulmonary nodule and the trachea and is related to the target pulmonary nodule are able to be extracted with high accuracy.

Note that, the fourth embodiment and the second embodiment may be combined. For example, though the decision boundary is provided in four sides of the composite masked image in FIG. 12 in the second embodiment, a side that serves as the decision boundary may be changed adaptively as in the fourth embodiment.

This makes it possible to achieve effects of both the second embodiment and the fourth embodiment.

Other Embodiment

While exemplary embodiments have been described in detail above, the present disclosure is able to be embodied as, for example, a system, an apparatus, a method, a program, or a recording medium (storage medium). More specifically, the present disclosure may be applied to a system configured by a plurality of devices (for example, a host computer, an interface device, an imaging apparatus, a web application, and the like) or may be applied to an apparatus configured by one device.

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While embodiments of the present disclosure have been described in detail above, the present disclosure is not limited to such specific embodiments and various modification and changes are possible within a scope of the gist of the present disclosure described in the claims.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2017-154671 filed Aug. 9, 2017, which is hereby incorporated by reference herein in its entirety.

What is claimed is:

1. An image processing apparatus comprising:
at least one memory; and
at least one processor functioning by executing instructions stored in the at least one memory as the following units:
a first extraction unit that extracts a region of a pulmonary nodule drawn in an image;
a second extraction unit that extracts a region of a structure drawn in the image;
a setting unit that sets a decision boundary to be at a position away from the pulmonary nodule region by a distance determined on a basis of a size of the pulmonary nodule region and a positional relationship between the pulmonary nodule and at least one of a lung field region and a region of trachea,
wherein the setting unit does not set the decision boundary in an opposite direction of a direction from the pulmonary nodule region toward the region of the trachea; and
an acquisition unit that acquires, as a region of a desired structure, the structure region which contacts with both the region related to the pulmonary nodule region and the decision boundary in the structure region extracted by the second extraction unit.

2. The image processing apparatus according to claim 1, wherein
the setting unit sets the decision boundary to be between the pulmonary nodule region and a trachea region.

3. The image processing apparatus according to claim 2, wherein the at least one processor further functions as:
a generation unit that generates, as a second image, a range that includes the pulmonary nodule region in the image and is determined on a basis of a size of the pulmonary nodule region, wherein
the setting unit sets the decision boundary to only an edge of a region located between the pulmonary nodule region and the trachea region in the second image.

4. The image processing apparatus according to claim 2, wherein the setting unit sets the decision boundary on a straight line connecting the pulmonary nodule region and the region of the trachea.

5. The image processing apparatus according to claim 1, wherein
the setting unit sets the decision boundary to be between the pulmonary nodule region and a region of an artery and vein in mediastinum.

6. The image processing apparatus according to claim 1, further comprising:
a generation unit that generates, as a second image, a range that includes the pulmonary nodule region in the image and is determined on a basis of a size of the pulmonary nodule region, wherein
the setting unit sets the decision boundary to an edge of the second image.

7. The image processing apparatus according to claim 1, wherein the at least one processor further functions as:
a third extraction unit that extracts a region of a trachea drawn in the image, wherein
the setting unit sets the decision boundary to be between the pulmonary nodule region extracted by the first extraction unit and the trachea region extracted by the third extraction unit.

8. The image processing apparatus according to claim 1, further comprising:
a third extraction unit that extracts a region of an artery and vein in mediastinum drawn in the image, wherein
the setting unit sets the decision boundary to be between the pulmonary nodule region extracted by the first extraction unit and the region of the artery and vein in the mediastinum extracted by the third extraction unit.

9. The image processing apparatus according to claim 1, further comprising:

a fourth extraction unit that extracts a region of a lung field drawn in the image, wherein
the setting unit sets the decision boundary on a basis of a position of the pulmonary nodule region extracted by the first extraction unit in the lung field region.

10. The image processing apparatus according to claim 1, wherein
the structure is a bronchus or an artery and vein.

11. The image processing apparatus according to claim 1, wherein the setting unit sets the decision boundary on a basis of (i) a value determined based on a plurality of images collected in advance and (ii) the size of the pulmonary nodule region.

12. The image processing apparatus according to claim 11, wherein the setting unit sets the decision boundary on a basis of (i) the size of the pulmonary nodule region in the plurality of images collected in advance and (ii) a value determined based on extraction accuracy of the region of the desired structure in the plurality of images collected in advance.

13. The image processing apparatus according to claim 12, wherein the setting unit uses, for setting the decision boundary, a value determined in advance such that the extraction accuracy of the region of the desired structure is high, in the plurality of images collected in advance, including a pulmonary nodule having a size that is substantially same as the size of the pulmonary nodule region drawn in the image.

14. The image processing apparatus according to claim 1, wherein the setting unit sets the decision boundary as a position, a direction and a range based on the positional relationship between the pulmonary nodule and at least one of the lung field region and the region of the trachea.

15. The image processing apparatus according to claim 1, wherein the setting unit sets a part of a surface of the figure as the decision boundary.

16. The image processing apparatus according to claim 1, wherein the setting unit sets the decision boundary in a predetermined direction based on information that defines a relative position of the pulmonary nodule in the lung field region and the region of the trachea.

17. The image processing apparatus according to claim 1, wherein the setting unit sets the decision boundary in the direction in which the bronchus is expected to run in terms of anatomical knowledge.

18. An image processing method comprising the steps of:
deciding whether or not a region of a structure drawn in an image contacts with both a region related to a region of a pulmonary nodule drawn in the image and a decision boundary that is set to be at a position away from the pulmonary nodule region by a distance determined on a basis of a size of the pulmonary nodule region;
wherein the decision boundary is not set in an opposite direction of a direction from the pulmonary nodule region toward the region of the trachea; and
acquiring, as a region of a desired structure, the structure region that is decided at the decision step to contact with both the pulmonary nodule region and the decision boundary in the structure region.

19. A non-transitory computer-readable storage medium storing a program causing a computer to execute an image processing method comprising the steps of:
deciding whether or not a region of a structure drawn in an image contacts with both a region related to a region of a pulmonary nodule drawn in the image and a decision boundary that is set to be at a position away from the pulmonary nodule region by a distance determined on a basis of a size of the pulmonary nodule region;
wherein the decision boundary is not set in an opposite direction of a direction from the pulmonary nodule region toward the region of the trachea; and
acquiring, as a region of a desired structure, the structure region that is decided at the decision step to contact with both the region related to the pulmonary nodule region and the decision boundary in the structure region.

20. An image processing apparatus comprising:
at least one memory; and
at least one processor functioning by executing instructions stored in the at least one memory as the following units:
a first extraction unit that extracts a region of a pulmonary nodule drawn in an image;
a second extraction unit that extracts a region of a structure drawn in the image;
a third extraction unit that extracts a second region drawn in the image, the second region being different from the pulmonary nodule region and the region of the structure;
a setting unit that sets a decision boundary between the pulmonary nodule region extracted by the first extraction unit and the second region extracted by the third extraction unit, wherein the setting unit does not set the decision boundary in an opposite direction of a direction from the pulmonary nodule region toward the region of the trachea;
a decision unit that decides whether or not the structure region extracted by the second extraction unit contacts with both (i) at least one of the pulmonary nodule region or an extension region obtained by expanding the pulmonary nodule region and (ii) the decision boundary; and
an acquisition unit that acquires, as a region of a desired structure, the structure region decided by the decision unit to contact with both (i) the at least one of the pulmonary nodule region or the extension region and (ii) the decision boundary.

* * * * *